US012760043B2

(12) United States Patent
Calogeropoulou et al.

(10) Patent No.: US 12,760,043 B2
(45) Date of Patent: Oct. 13, 2026

(54) COMPOUND FOR USE IN THE TREATMENT OF PROTOZOAL DISEASES AND PROCESS FOR PRODUCTION OF SAID COMPOUND

(71) Applicant: QUADREL S.R.L., Ozzano dell'Emilia (IT)

(72) Inventors: Theodora Calogeropoulou, Kifissia (GR); Kyriakos Prousis, Chalandri (GR); Marina Roussaki, Athens (GR); Georgios Magoulas, Glika Nera (GR); Theano Fotopoulou, Cholargos (GR)

(73) Assignee: QUADREL S.R.L., Ozzano dell'Emilia (IT)

( * ) Notice: Subject to any disclaimer, the term of this patent is extended or adjusted under 35 U.S.C. 154(b) by 624 days.

(21) Appl. No.: 18/246,084

(22) PCT Filed: Sep. 21, 2021

(86) PCT No.: PCT/EP2021/075969
§ 371 (c)(1),
(2) Date: Mar. 21, 2023

(87) PCT Pub. No.: WO2022/063790
PCT Pub. Date: Mar. 31, 2022

(65) Prior Publication Data

US 2023/0365602 A1 Nov. 16, 2023

(30) Foreign Application Priority Data

Sep. 22, 2020 (GR) ......................... GR20200100577

(51) Int. Cl.

| | |
|---|---|
| ***C07F 9/09*** | (2006.01) |
| ***A61K 45/06*** | (2006.01) |
| ***A61P 33/02*** | (2006.01) |

(52) U.S. Cl.
CPC ................ *C07F 9/09* (2013.01); *A61K 45/06* (2013.01); *A61P 33/02* (2018.01)

(58) Field of Classification Search
CPC ............. C07F 9/09; A61P 33/02; A61K 45/06
See application file for complete search history.

(56) References Cited

U.S. PATENT DOCUMENTS

2007/0167408 A1* 7/2007 Perrissoud et al.
2020/0093842 A1* 3/2020 MacLaughlan

FOREIGN PATENT DOCUMENTS

WO 2004041167 A2 5/2004

OTHER PUBLICATIONS

Calogeropoulou et al. (J. Med. Chem 2008, 51(4), 897-908) (Year: 2008).*
Kavian et al. (Acta Troica (2019); 196: 142-149) (Year: 2019).*
Mistry and Notman (J. Phys. Chem. B (2024); 128: 3885-3897) (Year: 2024).*

(Continued)

*Primary Examiner* — Brandon J Fetterolf
(74) *Attorney, Agent, or Firm* — Silvia Salvadori, P.C.; Silvia Salvadori

(57) ABSTRACT

The compound 5-cyclopentadecylpentyl (2-(trimethylammonio)ethyl) phosphate and pharmaceutical compositions thereof are provided for use in the treatment of a protozoal disease in a mammal. A process is also provided for the efficient, large-scale production of said compound.

16 Claims, 14 Drawing Sheets

(56) References Cited

OTHER PUBLICATIONS

Calogeropoulou et al. (J. Med. Chem. 2008; 51: 897-908) (Year: 2008).*
Calogeropoulou T. et al., “Design and synthesis of potent antileishmanial cycloalkylidene-subtitute ether phopholipid derivatives”, Journal of Medicinal Chemistry, vol. 51, No. 4, Feb. 1, 2008, pp. 897-908.
Search Report and Written Opinion of PCT/EP2021/075969 of Jan. 31, 2022.

* cited by examiner

COMPOUND FOR USE IN THE TREATMENT OF PROTOZOAL DISEASES AND PROCESS FOR PRODUCTION OF SAID COMPOUND

This application is a U.S. national stage of PCT/EP2021/075969 filed on 21 Sep. 2021, which claims priority to and the benefit Greek Patent Application No. GR20200100577 filed on 22 Sep. 2020, the contents of which are all incorporated herein by reference in their entireties.

TECHNICAL FIELD

The present invention relates to compound and compositions useful for the treatment of parasitic diseases of humans and animals for example leishmaniasis and Human African Trypanosomiasis (HAT). It also provides an efficient process for the synthesis of said compound.

BACKGROUND OF THE INVENTION

Protozoa are unicellular eukaryotes and represent one of most important sources of parasitic diseases. Every year, more than one million people die from complications from protozoal infections worldwide. Trypanosomatidae protozoa constitute the causative agents of several human diseases such as Chagas disease (*Trypanosoma cruzi*), sleeping sickness (*Trypanosoma brucei*) and leishmaniasis (*Leishmania* sp). The World Health Organization has classified these illnesses as neglected diseases, which affect people living in poverty in developing countries and for which no efficient therapy is available.

More specifically, leishmaniasis is a parasitic disease, which constitutes a major public health problem especially in the tropical and subtropical regions of the world. It is estimated that it causes 70000 deaths annually, a rate surpassed only by malaria among other parasitic diseases. It is currently endemic in 88 countries on five continents (Africa, Asia, Europe, and North and South America), and the population at risk reaches 350 million people. According to WHO, 12 million people are infected worldwide, with 2 million new cases per year. The distinguishable forms of the disease include visceral leishmaniasis (VL, or “kala-azar”), mucocutaneous leishmaniasis (MCL, ulceration of the skin and hyper development of the mucous membranes), and localized cutaneous and diffuse cutaneous leishmaniasis (CL and diffuse CL) and, if untreated, can have devastating consequences. Establishment of the infection and progression of the disease are favored by the compromised immune system of patients, like those infected with HIV, and as a result, *Leishmania*/HIV coinfection is now considered an extremely serious new disease with severe clinical, diagnostic, chemotherapeutic, epidemiological, and economic implications. Chemotherapy is currently the only way to treat the various forms of leishmaniasis in humans, since no human vaccine is yet available, however, the arsenal of drugs against the disease is still limited. Today, first line antileishmanial drugs are pentavalent antimonials (sodium stibogluconate and meglumine antimonate), which are slowly being replaced by liposomal amphotericin B, paromomycin or the first oral drug against the visceral form of the disease, miltefosine. However, all the aforementioned drugs have serious drawbacks such as toxicity, poor efficacy or high cost. In addition, the emergence of drug resistant parasites has complicated the current chemotherapeutic strategies and thus, the development of more effective and less toxic drugs is highly desirable (Burza S. et al; The Lancet 2018, 392, 951-970).

Canine leishmaniasis (CanL) caused by *L. infantum* or other *Leishmania* spp is a significant zoonosis, encountered in more than 70 countries worldwide and can be fatal to dogs. CanL is present in regions of southern Europe, Africa, Asia, South and Central America, while it has been reported also in the United States of America. In particular, in the Mediterranean basin it is estimated that close to 2.5 million dogs are infected. Dogs represent the main source of vector infection being the main domestic reservoirs. The chemotherapy of CanL includes mainly pentavalent antimonials, miltefosine and paromomycin. In addition, these are combined with immunomodulatory agents. Moreover, in veterinary medicine, allopurinol, a purine analog which inhibits purine biosynthesis, is considered for long-term treatment of CanL, in combination with a short treatment with pentavalent antimonials or miltefosine. However, resistance to allopurinol was recently reported. Finally, the available vaccines for CanL have low protective efficacy of about 68-71%.

Human African trypanosomiasis (HAT) (also known as sleeping sickness), another vector borne disease, is caused by *Trypanosoma brucei gambiense* or *Trypanosoma brucei rhodesiense* transmitted by tsetse flies (*Glossina* spp). HAT threatens more than 60 million people in a total of 36 countries in sub-Saharan Africa. The available treatments of HAT are few and restricted by low efficacy, toxicity, and long and cumbersome administration regimens, unsuitable for the infrastructure inadequacies in the remote rural regions affected by the disease (Keating J. et al; Acta Trop 2015, 150, 4-13.). Pentamidine and suramin are the treatment of choice for the hemolymphatic early stage of HAT caused by *T. b. gambiense*. Melarsoprol is the widely used treatment for the second meningoencephalitic stage caused by *T. b. rhodesiense* during which the parasite invades the central nervous system. However, the toxicity of the drug is usually fatal for the patients. Since 2009, nifurtimox is also used for the treatment of the second stage of the HAT, although it is not effective against *T. b. rhodesiense*. Recently the first oral treatment for HAT, fexinidazole, received a positive opinion from EMA for stage I and II.

At the moment fexinidazole is approved only in the Democratic Republic of Congo (2019) while, acoziborole is in clinical trials.

Miltefosine (hexadecylphosphocholine) constituted a major breakthrough in antileishmanial chemotherapy, since this compound is currently registered as an oral drug for the treatment of the disease in India (in 2002) and Colombia (in 2005). Despite its advantages, miltefosine has a long half-life (100-200 h) in humans and a low therapeutic ratio, characteristics that could favor the development of resistance, especially in India where VL is mainly an anthroponosis. Moreover, it is not suitable for pregnant women because it has been shown to cause teratogenesis in animals and it did not give satisfactory results when administered to HIV-coinfected patients, since most of them relapsed. Several potential mechanisms have been reported for the antileishmanial effect of miltefosine, indicating that it has more than one site of action, possibly also explaining the notable toxicity of this compound (Dorlo T. P. C. et al., J. Antimicrob Chemother 2012, 67, 2576-2597; Palić S. et al., Antimicrob Agents Chemother. 2019, 63, e02507-18). Therefore, new drugs are needed in the treatment of protozoal diseases and in particular leishmaniasis to overcome the significant side effects.

U.S. Pat. No. 8,097,752 discloses ring-containing phospholipids showing in vitro anti-leishmanial activity. Several preferred embodiments of that invention were synthesized and shown that they possess in vitro activity in the micromolar range. Thus, more potent compounds with better drug-like properties still need to be developed.

Publication J. Med. Chem. 2008, 51, 897-908 (Calogeropoulou T et al.) reports two series of ring-substituted ether phospholipid derivatives showing in vitro anti-leishmanial activity. The ring in the one series is a cyclodecylidene or a cyclopentadecylidene groups linked to the phosphate polar headgroup by an oligomethylene bridge of 5 or 11 carbons. The in vitro activity is studied against the promastigotes of *L. donovani* MON 703 and *L. infantum* MON 235 and against the intracellular amastigotes of *L. infantum* MON 235 in infected human monocytic THP-1 cells. In addition, the cytotoxicity of these compounds against THP-1 cells as well as their hemolytic activity in human erythrocytes was also studied.

The in vitro assays used to evaluate the potential compound activities do not reflect the complexity of the in vivo *Leishmania* infection (Yardley, V. & Koniordou, M. Drug Assay Methodology: From the Microplate to Image Analysis. In: Drug Discovery for Leishmaniasis, Carmen Gil, Luis Rivas (eds.) Royal Society of Chemistry, 2017). As a result, the efficacy in vitro does not guarantee activity in vivo, which depends on the complex drug pharmacokinetics, the site and the nature of the infection, and the ability of the drug to reach the site(s) of infection at effective concentrations (pharmacodynamics), to name a few. Thus, despite the fact that several of the reported compounds look promising when assessing their in vitro anti-leishmanial activity, the suitability of a compound for use in the treatment of Leishmaniasis, let alone its oral efficacy, cannot be determined without complex experimentation.

In the present invention, the inventors have unexpectedly shown that 5-cyclopentadecylpentyl (2-(trimethylammonio) ethyl) phosphate (originally described in Calogeropoulou T et al. J. Med. Chem. 2008, 51, 897-908 and hereinafter referred to as compound 19) is very active against leishmaniasis in animal studies, such as in mice, even when administered orally, and shows low toxicity, as demonstrated below. The in vitro efficacy against *leishmania* parasites for compound 19 and miltefosine is in the same range. Therefore, when in vivo pharmacology experiments were performed in comparative studies with miltefosine, it was an unexpected finding that compound 19 shows higher in vivo efficacy than miltefosine and is also substantially less toxic. Importantly, it is shown herein that compounds very similar to compound 19 (i.e. carrying small structural modifications) that are very potent in vitro against *Leishmania*, do not possess in vivo efficacy against the parasite.

An additional surprising finding is that compound 19, in contrast to miltefosine, is also active against *T. brucei* where it shows activity against stage I and most importantly against stage II of the infection. This means that compound 19 significantly reduces the parasite load in the brain.

SUMMARY OF THE INVENTION

The invention described herein addresses a need for effective and safe anti-leishmanial and antitrypanosomal compound which can be translated into drugs. It also provides an efficient, high-yield process for production of said compound, which greatly facilitates the industrial applicability of the present invention.

One aspect of this invention pertains to the compound 5-cyclopentadecylpentyl) (2-(trimethylammonio)ethyl) phosphate (19) for use in the prevention and/or treatment of protozoal diseases such as leishmaniasis and trypanosomiasis in a mammal.

A further aspect of this invention relates to a method for preventing and/or treating protozoal infections such as leishmaniasis and trypanosomiasis, which comprises administering an effective amount of the compound of the present invention to a mammal in need thereof.

In another aspect, a use of the compound of the present invention is provided for preventing and/or treating protozoal infections in a mammal.

Another aspect of the present invention is the provision of pharmaceutical compositions suitable for use in the prevention and/or treatment of protozoal diseases such as leishmaniasis and trypanosomiasis in a mammal.

In yet another aspect of the invention, said pharmaceutical compositions comprise 5-cyclopentadecylpentyl) (2-(trimethylammonio)ethyl) phosphate (19) and one or more active agents suitable for use in the prevention and/or treatment of protozoal diseases such as leishmaniasis and trypanosomiasis.

Another aspect of this invention relates to processes for the production of 5-cyclopentadecylpentyl) (2-(trimethylammonio)ethyl) phosphate (19) in high yield and purity.

Other aspects and further scope of applicability of the present invention will become apparent from the detailed description to follow.

BRIEF DESCRIPTION OF THE DRAWINGS

The present invention will now be described with reference to certain embodiments thereof, which are illustrated in the accompanying drawings. It should be noted that the accompanying drawings illustrate preferred embodiments of the invention, therefore should not be considered as limiting the scope of the invention.

DETAILED DESCRIPTION OF THE INVENTION

Figure 1A:
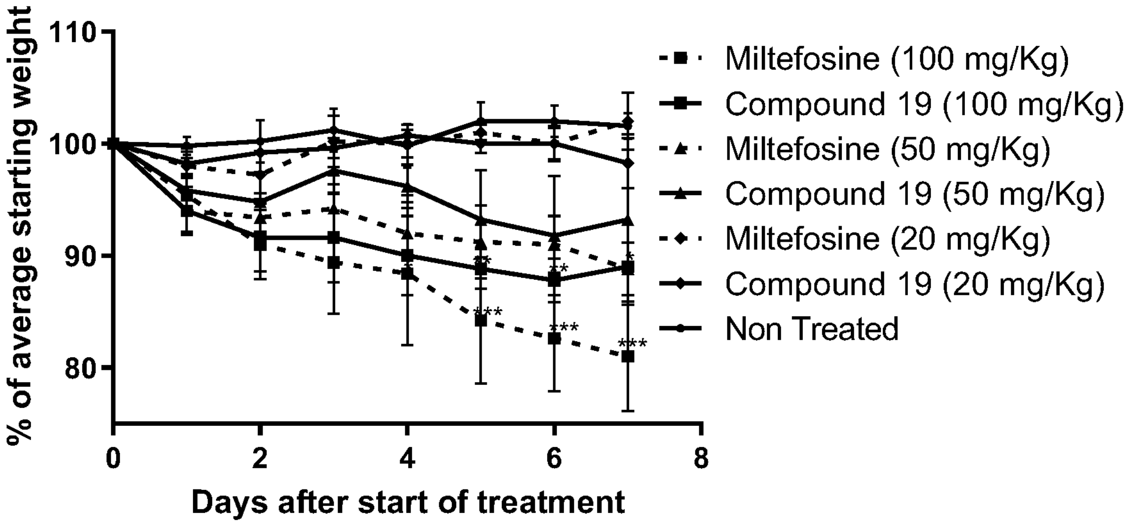
FIG. 1 illustrates the changes in food intake and weight variation associated to the dose range finding study in rodents. (A) Average food intake (±SD) for the duration of the experiment, each point represents the registered daily food uptake. *$P<0.05$; $P<0.01$; *$P<0.001$ as determined by Bonferroni's Multiple Comparison Test for comparison with non-treated group. (B) Average weight loss (±SD) associated to the treatments for the duration of the experiment. *$P<0.05$; $P<0.01$; *$P<0.001$ as determined by Bonferroni's Multiple Comparison Test.

Unless defined otherwise, all technical and scientific terms used herein have the same meaning as commonly understood by those of ordinary skill in the art considering the present disclosure and context.

As used herein, the terms "therapeutic", "treatment" and "treating" refer to the elimination, reduction, suppression, inhibition of the progression, severity, and/or scope of a disease, lesion, clinical sign or symptom in a subject. Said terms also refer to the alleviation, in whole or in part, of clinical signs and symptoms associated with a disorder or disease such as, for instance, leishmaniasis or trypanosomiasis.

The terms "prevention", "preventive", "prophylaxis" and "prophylactic" as used herein, refer to the reduction in the risk of acquiring or developing a disease or disorder, for instance in subjects who are susceptible to the disease (e.g. members of a particular population, those with risk factors, or at risk for developing the disease). These terms may also refer to the reduction or inhibition of the recurrence or the spread of the disease or disorder e.g. leishmaniasis or trypanosomiasis.

As used herein, a "treatment course" relates to the duration of a particular treatment or therapeutic regimen.

"Intralesional administration" as used herein, means that the compound or composition of the invention is administered at the sites of parasite-caused lesions of patients, such as the skin lesions in case of *Leishmania* or *Trypanosoma* infections.

The t max (time of peak plasma concentration) is the time required to reach maximum drug concentration in the plasma after drug administration. In other words, t max is peak plasma time, also defined as the time to reach C max. C max is the maximum (peak) plasma drug concentration attained after the oral administration of the drug.

The t½ (elimination half-life) is the time required to decrease the drug concentration in plasma by one-half during elimination. In other words, t½ (elimination half-life) is the time required for the amount or concentration of a drug to decrease by one-half.

The inventors have unexpectedly found that 5-cyclopentadecylpentyl (2-(trimethylammonio) ethyl) phosphate (19) presented oral availability (as determined by snapshot pharmacokinetic, SNAP-PK) and also was bio-accumulated in the spleen and liver, which are the target organs for visceral leishmaniasis. Significantly, compound 19 effectively maintains parasite burden under the detection limit in BALB/c mice experimentally infected with *L. infantum* when administered by oral gavage for 21 days, being superior to the oral standard-of-care, miltefosine. Similarly, treatment with compound 19 for 10 consecutive days is more effective than miltefosine in reducing parasite burden in the liver and spleen.

Also significantly, no major toxicity was found during the in vivo assays (as determined by evaluation of general health status, blood parameters and routine biochemistry analysis-hepatic and renal parameters) in BALB/c mice infected with *L. infantum*. Also comparative non-regulatory toxicity assays in BALB/c mice suggest that miltefosine is more toxic than compound 19 (maximum tolerated dose in a 7 day toxicity assay was 50 mg/kg for miltefosine and 100 mg/kg for compound 19). Therefore, the data on 5-cyclopentadecylpentyl (2-(trimethylammonio) ethyl) phosphate (19) fully support it as a more active and less toxic alternative to miltefosine for the treatment of leishmaniasis in humans and other mammals.

Thus, 5-cyclopentadecylpentyl (2-(trimethylammonio) ethyl) phosphate (19) has a balance of efficacy and toxicity superior to that of the currently available oral treatment, miltefosine.

In addition, 5-cyclopentadecylpentyl (2-(trimethylammonio) ethyl) phosphate (19) was effective per os in vivo against *T. brucei* acute model of infection and also against the long lasting chronic infection model. This activity was shown by full clearance of infection in an acute BALB/c *T. b. brucei* infection model using a daily treatment of 50 mg/kg (per os) for 7 consecutive days. Miltefosine showed no in vivo activity using the same treatment schedule. 5-cyclopentadecylpentyl (2-(trimethylammonio) ethyl) phosphate (19) also proved active in another mice model that is representative of an acute *T. b. brucei* infection with dissemination to the central nervous system. The daily treatment with 50 mg/kg for 13 days lead to a significant decrease of infection and increase in animal survival. Significantly this decrease was also found in the central nervous system as seen by the decrease of parasite signal in the brain. When compared to the beginning of treatment (day 21), compound 19 induced an average reduction of signal (average radiance) in the brain region of 99.96%. This reduction was fast, since after just 4 treatments (day 25) 99.95% of the signal in the region of the brain was lost. Moreover the continuous overtime decrease of the signal during the treatment of the animals suggests that treatment optimization might enable full clearance of the infection. Altogether 5-cyclopentadecylpentyl (2-(trimethylammonio) ethyl) phosphate (19) is effective in the BALB/c infection model for *T. brucei* being a possible therapeutical option both for HAT stage I and II.

Importantly, the inventors have shown that even small changes in the chemical structure of the compound may have detrimental effects on its potency in vitro against various protozoa, its pharmacokinetic characteristics and/or its in vivo efficacy against protozoal infections. Therefore, these data support the evidence that the compound 5-cyclopentadecylpentyl (2-(trimethylammonio)ethyl) phosphate (19) is structurally optimized for use in the treatment of protozoal diseases.

Thus, a first aspect of the present invention provides the compound 5-cyclopentadecylpentyl (2-(trimethylammonio) ethyl) phosphate (19), its stereoisomers, polymorphs or the physiologically acceptable salts thereof, for use in the prevention and/or treatment of a protozoal disease in a mammal. Suitable physiologically acceptable salts of compound 19 may include phosphocholine chloride calcium salt tetrahydrate or the salts formed with sodium chloride among others.

The protozoal diseases (or protozoal infections) that can be prevented or treated in accordance with the use described herein include leishmaniasis, acute and chronic cutaneous leishmaniasis, visceral leishmaniasis, also known as kala-azar, mucocutaneous leishmaniasis, canine leishmaniasis, trypanosomiasis, African trypanosomiasis, stage I human African Trypanosomiasis, stage II human African Trypanosomiasis, animal trypanosomiasis, Chagas disease, malaria, toxoplasmosis, babesiosis, amoebic dysentery, schistosomiasis, *theileria* infections, neosporosis and giardiasis.

A preferred embodiment provides the compound 5-cyclopentadecylpentyl (2-(trimethylammonio)ethyl) phosphate (19), its stereoisomers, polymorphs or the physiologically acceptable salts thereof, for use in the prevention and/or treatment of leishmaniasis in a mammal, including, but not limited to, acute and chronic cutaneous leishmaniasis, visceral leishmaniasis, also known as kala-azar, mucocutaneous leishmaniasis and canine leishmaniasis.

Unlike miltefosine, compound 19 is also effective orally in the treatment of stage I and stage II African trypanosomiasis. Most importantly, compound 19 significantly reduced the parasite load in the brain, while pentamidine administered intraperitoneally is not effective. Therefore, another preferred embodiment provides the compound 5-cyclopentadecylpentyl (2-(trimethylammonio)ethyl) phosphate (19), its stereoisomers, polymorphs or the physiologically acceptable salts thereof, for use in the prevention and/or treatment of trypanosomiasis, including, but not limited to, African trypanosomiasis, stage I human African Trypanosomiasis, stage II human African Trypanosomiasis, animal trypanosomiasis and Chagas disease.

A mammal includes but is not limited to a human, mouse, rat, hamster, guinea pig, dog, cat, equid such as a horse, cow, pig, rabbit or non-human primate, such as a monkey, chimpanzee, baboon or gorilla. In certain embodiments, the subject is a human. In certain embodiments, the subject is a non-human mammal. In preferred embodiments, the non-human mammal is a dog.

Any suitable route of administration may be used, as determined by a treating physician or veterinarian, including, but not limited to, oral, intranasal, parenteral, transdermal, topical administration, intralesional or rectal administration route. The term “parenteral” as used herein includes subcutaneous, intravenous, intraarterial, intramuscular, intraperitoneal, intrathecal, intraventricular, intrasternal, intracranial, and intraosseous injection and infusion techniques. The preferred administration route is oral, intranasal, intravenous, topical or intralesional. As shown in the examples therein, the compound of the present invention shows high bioavailability and efficacy against protozoal infections even when administered orally, and this is a clear advantage compared to the majority of the anti-leishmanial and anti-*trypanosoma* drugs that require intravenous administration. The intranasal route is a minimally invasive drug administration pathway, which bypasses the blood-brain barrier, making it suitable for certain applications, such as for the administration of compound 19 to the central nervous system for the treatment of stage II African trypanosomiasis. Most preferably, the compound is administered orally.

According to certain embodiments, the compound is administered to the subject in a prophylactic course. A suitable duration of prophylactic course may be from 1 day to 5 days long, preferably from 1 day to 3 days long.

According to certain embodiments, the compound is administered to the subject in a treatment course. A suitable duration of treatment course may be from 1 day to 30 days long, preferably from 3 days to 28 days long. In certain embodiments, the treatment course is short, for instance from 3 days long to 10 days long, preferably from 3 to 7 days long. In other embodiments, the treatment course is long, for instance from 15 to 28 days long, preferably from 21 to 28 days long.

The subject may be treated daily for the whole duration of the prophylactic course or the treatment course. Based on preliminary PK data shown herein, the amount of compound 19 remains high after 48 hours and also that the compound shows high bio-accumulation in the kidneys, therefore a treatment scheme of every other day or every third day may be used instead.

For prophylactic or therapeutic administration of compound 19, the dose ranges from about 0.1 mg/kg/day to 100 mg/kg/day of body weight. Preferred dosage regimens for the compound of the invention range from 1 mg/kg/day to 50 mg/kg/day via oral administration. For example, the dosage regimens can be 2.5 mg/kg/day body weight, 5 mg/kg/day body weight, 10 mg/kg/day body weight, 15 mg/kg/day body weight, 20 mg/kg/day body weight or 50 mg/kg/day body weight. The daily dose can be administered as a single dosage or in divided dosages, preferably 2 or 3 dosages per day.

It will be appreciated that for administration to neonates, young animals or children, lower doses may be required. In the case of neonates, the dose may be approximately four times less than for an adult, and in the case of young children (4-6 years old), the dose may be approximately half the dose used for an adult.

In certain embodiments, the doses of compound 19 administered on a prophylactic course are within the range from 20 mg/kg/day body weight to 50 mg/kg/day body weight.

In some embodiments, high doses of compound 19 are administered on a short treatment course. In these embodiments, a high dose such as, for instance, 50 mg/kg/day per os (PO) is administered on a treatment course of 3 or 7 days for instance. In some embodiments, low doses of compound 19 are administered on a long treatment course. In these embodiments, a low oral dose such as, for instance, 2.5 mg/kg/day, 5 mg/kg/day, 10 mg/kg/day or 20 mg/kg/day is administered on a treatment course of 21 or 28 days for instance.

According to the invention, exemplary preferred prophylactic regimens include oral administration of 50 mg/Kg/day every day for 1 to 3 days. Exemplary preferred treatment regimens include a) oral administration of 2.5, 5, 10 or 20 mg/Kg/day every other day for 21 days, b) oral administration of 2.5, 5, 10 or 20 mg/Kg/day every day for 10 days, c)

oral administration of 10 mg/Kg/day or 20 mg/Kg/day every day for 5 consecutive days, d) oral administration of 2.5, 5, 10 or 20 mg/Kg/day every day for 28 consecutive days.

A certain embodiment provides compound 5-cyclopentadecylpentyl (2-(trimethylammonio)ethyl) phosphate (19) for use in the prevention and/or treatment of African Trypanosomiasis, wherein said compound is administered to the subject at a dose within the range from 20 mg/kg/day to 100 mg/kg/day bodyweight. Preferably compound 19 is administered at a dose within the range from 20 mg/kg/day to 60 mg/kg/day bodyweight, most preferably 50 mg/kg/day bodyweight. The treatment may be administered over a period ranging from 3 to 10 days, preferably for a period ranging from 3 to 7 days.

The effects of any particular dosage regimen can be monitored by a suitable bioassay. For instance, parasite load of patients with cutaneous leishmaniasis may be determined in skin biopsies using real-time quantitative PCR; detection of anti-*Leishmania* antibodies may be performed using IFAT and ELISA. The dosage can be adjusted by the attending physician or veterinarian if necessary, taking into consideration the observed effects of the treatment.

A further aspect of this invention relates to a method for preventing and/or treating protozoal infections such as leishmaniasis and trypanosomiasis, which comprises administering an effective amount of compound 5-cyclopentadecylpentyl (2-(trimethylammonio)ethyl) phosphate (19), its stereoisomers, polymorphs or the physiologically acceptable salts thereof, to a mammal in need thereof.

In another aspect, a use of compound 5-cyclopentadecylpentyl (2-(trimethylammonio)ethyl) phosphate (19), its stereoisomers, polymorphs or the physiologically acceptable salts thereof, is provided for preventing and/or treating protozoal infections in a mammal.

A further aspect of the invention provides pharmaceutical compositions comprising compound 5-cyclopentadecylpentyl (2-(trimethylammonio)ethyl) phosphate (19), its stereoisomers, polymorphs or the physiologically acceptable salts thereof, and a pharmaceutically acceptable carrier, for use in the treatment of a protozoal disease in a mammal.

The protozoal diseases (or protozoal infections) that can be prevented and/or treated in accordance with the use described herein include leishmaniasis, acute and chronic cutaneous leishmaniasis, visceral leishmaniasis, also known as kala-azar, mucocutaneous leishmaniasis, canine leishmaniasis, trypanosomiasis, African trypanosomiasis, stage I human African Trypanosomiasis, stage II human African Trypanosomiasis, animal trypanosomiasis, Chagas disease, malaria, toxoplasmosis, babesiosis, amoebic dysentery, schistosomiasis, *theileria* infections, neosporosis and giardiasis.

According to a preferred embodiment, the pharmaceutical compositions of the invention are provided for use in the prevention and/or treatment of leishmaniasis in a mammal.

According to another preferred embodiment, the pharmaceutical compositions of the invention are provided for use in the prevention and/or treatment of stage I and/or stage II African trypanosomiasis in a mammal.

A mammal includes but is not limited to a human, mouse, rat, hamster, guinea pig, dog, cat, equid such as a horse, cow, pig, rabbit or non-human primate, such as a monkey, chimpanzee, baboon or gorilla. In certain embodiments, the subject is a human. In certain embodiments, the subject is a non-human mammal. In preferred embodiments, the non-human mammal is a dog.

Any suitable route of administration may be used for the pharmaceutical compositions of the invention, as determined by a treating physician or veterinarian, including, but not limited to, oral, intranasal, parenteral, transdermal, topical administration, intralesional or rectal administration route. Intralesional administration may preferably be performed via intralesional injection or infusion. The term "parenteral" as used herein includes subcutaneous, intravenous, intraarterial, intramuscular, intraperitoneal, intrathecal, intraventricular, intrasternal, intracranial, and intraosseous injection and infusion techniques. The preferred administration route is oral, intravenous, intranasal, topical or intralesional. Most preferably, the compositions are administered orally. For oral administration, the pharmaceutical compositions can be provided in the form of tablets, coated tablets, granules, hard and soft gelatin capsules, solutions, syrups, emulsions, suspensions or aerosol mixtures. For the solid dosage forms, the compositions may be formulated as an immediate release dosage form, a delayed release dosage form, or an extended release dosage form, for instance.

Formulations for oral administration in solid or liquid form can be prepared according to any method known in the manufacture of pharmaceutical compositions and such compositions may contain one or more agents selected from the group comprising preservatives, wetting or emulsifying agents, pH buffering agents, stabilizers, detergents, antioxidants, carriers, flavoring agents, phospholipids, fillers, disintegrants, binders, lubricants, stabilizers, sweeteners, colorants, thickening agents, solvents, solubilizers, agents for generating sustained release tablets, salts for varying the osmotic pressure, coating agents, and other factors. The tablets may be uncoated or may be coated by known techniques. In some cases, such coatings can be prepared by known techniques to delay disintegration and absorption in the gastrointestinal tract and thereby provide a sustained action over a longer period. For example, a time delay material may be used such as monoglycerides or diglycerides of stearic acid. Suitable excipients for the production of solutions, for example of emulsions or syrups are, for example, water, saline, alcohols, glycerol, polyols, sucrose, invert sugar, glucose, vegetable oils, and others.

Formulations suitable for intranasal administration may include physiologically acceptable sterile aqueous or non-aqueous solutions, liquid formulations, dispersions, semi-solid or particulate formulations, suspensions or emulsions. The formulations may also comprise adsorption enhancers for improved permeation and absorption, such as cyclodextrins, bile salts, laureth-9 sulfate, fusidate derivates, fatty acids, hydrophilic polymers, surfactants etc.

For intravenous, cutaneous or subcutaneous injection, or intralesional injection, dosage forms may be prepared in the form of sterile or sterilizable injectable preparations such as injectable solutions, suspensions, dry and/or lyophylized products ready to be dissolved or suspended in a pharmaceutically acceptable vehicle for injection (reconstitutable powders) and emulsions. Among the acceptable vehicles and solvents that can be employed are water, dextrose, Ringer's solution and isotonic sodium chloride solution, water-miscible vehicles such as, but not limited to, ethyl alcohol, polyethylene glycol, and polypropylene glycol; and non-aqueous vehicles such as, but not limited to, vegetable oils (e.g. corn oil, cottonseed oil, sesame oil), injectable organic esters such as ethyl oleate and isopropyl myristate, and benzyl benzoate. Preservatives, stabilizers, buffers, antioxidants and/or other additives may be included, as required.

Topical formulations include solutions, lotions, creams, ointments, gels, pastes, solids, aerosols or patches. Solutions may be water- or alcohol-based. Lotions may contain oil with water or alcohol, emulsifying agents or other suitable stabilizers. Creams are thicker than lotions, for example may comprise a 50/50 emulsion of oil and water, varied oils/butters, moisturizers and preservatives. Ointments are water-free or nearly water-free and may include a hydrocarbon (paraffin), wool fat, beeswax, macrogols, emulsifying wax, cetrimide or vegetable oil (olive oil, *arachis* oil, coconut oil). Gels are aqueous or alcoholic monophasic semisolid emulsions, often based on cellulose, and may also include preservatives and fragrances. Pastes are usually concentrated suspension of oil, water and powder. Aerosols (foam or spray) contain solutions with pressurised propellant. Solid topical formulations may for example contain talc or corn starch.

A delivery system can be used in order to further enhance stability of the compound, increase bioavailability, modify drug release profile, increase solubility, decrease adverse effects, achieve tissue targeting, and/or increase patient compliance. Examples of drug delivery systems include nanoparticles, liposomes, niosomes, microspheres or nanotubes. Nanoparticles featuring spherical morphology and sub-micrometric diameter (1-1,000 nm) can be used to incorporate one or more active compounds, thus serving as drug carriers. Polymeric nanoparticles include systems such as nanospheres, nanocapsules, polymeric micelles, dendrimers, nanogels, polymersomes or polymer-modified nanocarriers. Lipid nanocarriers, namely solid lipid nanoparticles, nanostructured lipid carriers and liposomes can also be used as carriers for active compounds. Nanocarriers of mixed nature, for example combining different polymers and/or lipids, can also be used. Polymers of synthetic or natural origin, either biodegradable or not, are used to produce nanoparticles, including polyesters (various grades of poly (lactide-co-glycolide), poly(lactide), poly(beta-hydroxybutyric acid), poly(beta-hydroxyvaleric acid) and polycaprolactone), polyacrylates, poly(alkyl cyanoacrylates), polyanhydrides, polyphosphoesters, poly-L-lysine, poly(ortho esters), polyphosphazenes, poly(amidoamine), polysaccharides (for example, various grades of chitosan, alginates, cellulose derivatives), and proteins (for example, albumin and gelatin), among others. Copolymers of poly(ethylene glycol) (PEG) or poly(ethylene oxide) (PEO) may also be used, namely PEG/PEO-b-poly(3-[(3-aminopropyl)amino] propylaspartamide), PEG/PEO-b-poly(amino acids), PEG/PEO-b-poly[(2-dimethylamino)ethyl methacrylate], PEG/PEO-b-poly(alpha,beta-aspartic acid), PEG/PEO-b-P(Asp) processing the hydrazide groups in the side chains, PEG/PEO-b-poly(beta-benzyl L-aspartate), PEG/PEO-b-PCL, PEG/PEO-b-PLA, PEG/PEO-b-phosphatidylethanolamine, PEG/PEO-b-polyethylethylene, PEG/PEO-b-poly(glutamic acid), PEG/PEO-b-poly(I-histidine) or PEG/PEO-b-PLGA. Materials used for producing nanoparticles of lipid-origin include phosphatidylcholine, cholesterol, stearylamine, dilauroylphosphatidylcholine, dipalmitoyl-phosphatidylcholine, 1,2-dioleoyl-sn-glycero-3-phosphocholine, dimyristoylphosphatidic sodium, 1,2-dioleoyl-3-trimethylammoniumpropane, N-[2,3-(dioleyloxy)propyl]-N,N,N-trimethylammonium chloride, 3-β-[N—(N',N'-dimethylaminoethyl) carbamoyl]-cholesterol, 2,3-dioleyloxy-N-[2(spermine-carboxamido)ethyl]-N,Ndimethyl-1-propanaminium trifluoroacetate, dioleoyl phosphatidylethanolamine, oleic acid, cholesteryl hemisuccinate, dipalmitoyl phosphatidylcholine, tricaprin, trilaurin, tripalmitin, cetyl palmitate, glycerol behenate, glycerol palmitostearate, cetyl palmitate, among others, used alone or typically in suitable mixtures. Stabilizers are frequently used in order to allow nanoparticle production. These last include lecithin of different origins, poloxamers of different grades, sodium cholate, poly(vinyl alcohol) of different grades, sodium lauryl sulfate, cetrimide, cetyl trimethylammonium bromide, polysorbates of different grades, among others.

The compounds of the invention can be formulated in combination with one or more absorption enhancers. Absorption enhancers can particularly be used to increase the flux of the compound across the skin or to target the lymphatic system. Suitable absorption enhancers include, but are not limited to, sodium glycocholate, sodium salicylate-chenodeoxycholate, taurodeoxycholate, ceramide analogs, azone analogs, terpenes, sodium caprate, N-lauryl-β-D-maltopyranoside, EDTA, or polymeric absorption enhancers.

Pharmaceutical compositions of the invention also can be administered in combination therapy, i.e., combined with one or more additional active substances. In some embodiments, the one or more additional active substances are used in the treatment of protozoal diseases. The one or more additional active substances in preferred embodiments may be selected from the group consisting of pentavalent antimonial preparations, amphotericin B, suramin, pentamidine and derivatives, allopurinol, melarsoprol, benznidazol, nifurtimox, ketoconazol, difluoromethylornithine, chloroquine and their derivatives, quinine, immunostimulants and immunomodulatory agents.

Combination therapy according to the present invention may include both fixed and non-fixed combinations of the active ingredients. The term non-fixed combination or "kit" means that the active ingredients are administered to a patient as separate entities either simultaneously or sequentially with no specific time limits. The term "fixed dose combination" means that the active ingredients are administered to a patient simultaneously in the form of a single entity or dosage. When drugs are administered as a fixed dose combination, the dosage form and administration route should be selected depending on the compatibility of the combined drugs.

The fixed dose combination may for instance be formulated as solid dosage forms, such as immediate release dosage forms, delayed release dosage forms, extended release dosage form, or as dosage forms comprising an immediate release component with the one active ingredient and an extended release component with the other active ingredient (such as a bi-layer tablet), for instance.

The inventors have surprisingly observed that compound 5-cyclopentadecylpentyl (2-(trimethylammonio) ethyl) phosphate (19) aggregates in saline solutions of NaCl producing a homogeneous gel product at concentrations between 7 and 40 mg/mL at temperature range between 20° C. and 40° C., preferably at ambient temperature. The homogeneity of the product facilitates homogeneity of dosing, i.e., variability among doses is lower, enabling easy administration of the compound and higher patient acceptability. This gel formation was not observed at the same conditions with other similar molecules such as miltefosine.

Yet another aspect of the invention provides an efficient, high-yield process for the production of 5-cyclopentadecylpentyl (2-(trimethylammonio)ethyl) phosphate (19), said process comprising the following steps:

a) cyclopentadecanone is added to a mixture of (4-carboxybutyl)triphenylphosphonium bromide and a base, to yield the corresponding Wittig product;
b) the Wittig product of step (a) is allowed to react with a reducing agent to form the corresponding unsaturated alcohol;

c) the resulting unsaturated alcohol is hydrogenated to the respective saturated alcohol under hydrogen atmosphere, and d) a mixture of phosphoryl chloride and a base is added to the saturated alcohol of step (c); the resulting phosphoric acid is reacted with a base, to form the corresponding salt which in turn reacts with a condensing agent and a choline salt to form the title compound. Alternatively, d') phosphoryl chloride is reacted with 1,2,4-triazole in the presence of a base, followed by a mixture of bases and the saturated alcohol of step (c). Subsequently a choline salt, preferably choline p-toluenesulfonate or choline tetraphenylborate is added to form the title compound.

Preferably, said process for the production of 5-cyclopentadecylpentyl (2-(trimethylammonio)ethyl) phosphate (19) comprises the following steps:

a) cyclopentadecanone (1 equivalent) is added to a mixture of (4-carboxybutyl)triphenylphosphonium bromide (2 to 3 equivalents, preferably 2 equivalents) and a base, preferably potassium tertiary butoxide (4 to 6 equivalents, preferably 4 equivalents), to yield the corresponding Wittig product;

b) the Wittig product of step (a) (1 equivalent) is allowed to react with a reducing agent preferably lithium aluminium hydride (1 to 4 equivalents, preferably 3.2 equivalents), to form the corresponding unsaturated alcohol;

c) the resulting unsaturated alcohol is hydrogenated to the respective saturated alcohol under hydrogen atmosphere, and d) a mixture of phosphoryl chloride (1 equivalent) and a base (1 to 5 equivalents) preferably triethylamine is added to the saturated alcohol of step (c) (0.5 to 1 equivalent); the resulting phosphoric acid is reacted with a base, preferably pyridine, to form the corresponding salt which in turn reacts with a condensing agent (1 to 3 equivalents), preferably mesitylene nitro triazolide and a choline salt (1 to 3 equivalents), preferably choline p-toluenesulfonate or choline tetraphenylborate, to form the title compound. Alternatively, d') phosphoryl chloride (1 equivalent) is reacted with 1,2,4-triazole (3 to 4 equivalents) in the presence of a base (2 to 4 equivalents), preferably DIPEA, followed by a mixture of bases (0.50 to 3 equivalents) preferably DMAP or DIPEA or pyridine and the saturated alcohol of step (c) (0.5 to 1 equivalent). Subsequently a choline salt (1 to 3 equivalents), preferably choline p-toluenesulfonate or choline tetraphenylborate, is added to form the title compound.

EXAMPLES

Hereinafter, the present invention is described in more detail with reference to examples and comparative examples. It will be apparent to one of ordinary skill in the art that these examples are for illustrative purposes only and should not be construed as limiting or altering the scope of the present invention.

General Methods

All starting materials and common laboratory chemicals were purchased from commercial sources and used without further purification. All reactions were carried out under scrupulously dry conditions. $^{1}H$ NMR spectra were recorded on Varian spectrometers operating at 600 or 300 MHz, $^{13}C$ and $^{31}P$ spectra were recorded at 150 or 75 MHz and 121 MHz respectively, using $CDCl_3$ or $CD_3OD$ as solvents. Chromatographic purification was performed with silica gel (200-400 mesh). Mass spectra were obtained on HPLC-MS$^n$ Fleet-Thermo, in the ESI mode. HRMS spectra were recorded, in the ESI mode, on UPLC-MS$^n$ Orbitrap Velos-Thermo. The purity of the tested compounds was determined by HPLC (Thermo Scientific HPLC Spectra System) column Atlantis HILIC Silica 3 μm, 4.6×100 mm.

Synthetic Procedures

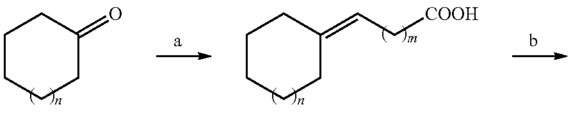

1: n = 7
2: n = 10

3: n = 7, m = 2
4: n = 7, m = 3
5: n = 10, m = 2
6: n = 10, m = 3

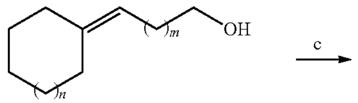

7: n = 7, m = 2
8: n = 7, m = 3
9: n = 10, m = 2
10: n = 10, m = 3

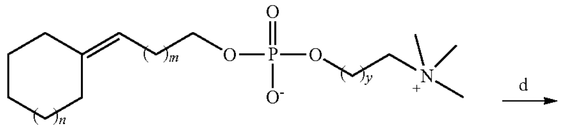

11: n = 7, m = 2, y = 1
12: n = 7, m = 3, y = 1
13: n = 10, m = 2, y = 1
14: n = 10, m = 3, y = 1
15: n = 10, m = 3, y = 2

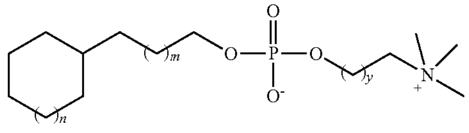

16: n = 7, m = 2, y = 1
17: n = 7, m = 3, y = 1
18: n = 10, m = 2, y = 1
19: n = 10, m = 3, y = 1
20: n = 10, m = 3, y = 2

The above process describes the chemical synthesis of compound 19 and Comparative Examples 1-7. Reagents and conditions: (a) $HOOC(CH_2)_4Ph_3P^+Br^-$ or $HOOC(CH_2)_4Ph_3P^+Br^-$ or $MeOOC(CH_2)_{10}Ph_3P^+Br^-$, $[(CH_3)_3Si]_2NK$, THF, rt, overnight; (b) $LiAlH_4$, THF, rt, 2 h; (c) (1) $POCl_3$, $Et_3N$, THF, −5° C., 15 min then $H_2O$, 30 min; (2) Pyridine, 45° C., 2.5 h; (3) Pyridine, choline tosylate, MSNT, 0° C. then rt, 24 h; (d) $H_2$, Pd/C, MeOH, overnight; (e) $(EtO)_2P(O)CH_2CO_2Et$, NaH, THF, rt, overnight.

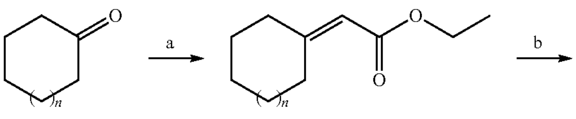

1: n = 7
2: n = 10

21: n = 7
22: n = 10

-continued

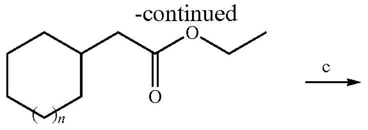

23: n = 7
24: n = 10

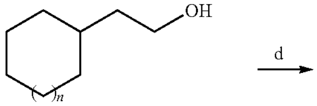

25: n = 7
26: n = 10

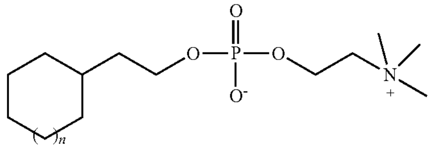

27: n = 7
28: n = 10

The above process describes the chemical synthesis of Comparative Examples 8 and 9. Reagents and conditions: (a) $(EtO)_2P(O)CH_2CO_2Et$, NaH, THF, rt, overnight. (b) $H_2$, Pd/C, MeOH, overnight; (c) $LiAlH_4$, THF, rt, 2 h; (d) (1) $POCl_3$, $Et_3N$, THF, −5° C., 15 min then $H_2O$, 30 min; (2) Pyridine, 45° C., 2.5 h; (3) Pyridine, choline p-toluenesulfonate, MSNT, 0° C. then rt, 24 h.

General procedure (A) for the Wittig reaction for the synthesis of compounds 3-6. To an ice-cold solution of (3-carboxypropyl) triphenylphosphonium or (4-carboxybutyl)triphenylphosphonium bromide (2 mmol) in THF (6 mL), potassium bis(trimethylsilyl) amide (4 mmol) was added and the mixture was stirred for 30 minutes at rt. Then a solution of cyclododecanone (1) or cyclopentadecanone (2) (1 mmol) in THF (7 mL) was added dropwise and the reaction was stirred at rt overnight. The solvent was removed in vacuo and the mixture was diluted with water and washed with $Et_2O$. The mixture was then acidified to pH 2 and extracted with DCM, dried over $Na_2SO_4$ and evaporated to dryness. Pure unsaturated acids were obtained after flash column chromatography.

General procedure (B) for the preparation of alcohols 7-10. To an ice-cold suspension of $LiAlH_4$ (0.083 g, 2.2 mmol) in dry THF (6.0 mL), a solution of acid 3, 4, 5 or 6 (1.0 mmol) in dry THF (6.0 mL) was added dropwise. The resulting mixture was stirred at ambient temperature for 2 h. Subsequently, the reaction mixture was quenched at 0° C. by a mixture THF/$H_2O$ (1:1) and finally $H_2O$. The solids were filtered off, and the filtrate was diluted with EtOAc. The organic layers were washed twice with $H_2O$, dried over $Na_2SO_4$ and evaporated to dryness. Pure alcohols 7-10 were obtained after flash column chromatography.

General Procedure (C) for the Preparation of Ether Phospholipids 11-15, 27 and 28. To an ice-cold solution of $POCl_3$ (0.09 ml, 1 mmol) and $Et_3N$ (0.25 mL, 1.8 mmol) in THF (5 mL), a solution of the corresponding alcohol 7, 8, 9, 10, 25 and 26 (1 mmol) in THF (7 mL) was added dropwise. The mixture was stirred at ambient temperature for 2 h, and then H2O (5 mL) was added and stirring was continued for 1 h. The aqueous layer was extracted first with EtOAc and then with $CH_2Cl_2$. The combined organic extracts were dried over anhydrous $Na_2SO_4$ and the solvent was evaporated in vacuo to afford the corresponding phosphoric acid derivative, which was transformed to the pyridinium salt upon the addition of 5 mL of anhydrous pyridine and stirring for 2 h at 40° C. Then, the mixture was left to attain ambient temperature and it was evaporated under vacuo. To an ice-cold solution of the above salt (1 mmol) in pyridine (7 ml) was added portionwise 1-(mesitylen-2-sulfonyl)-3-nitro-1H-1,2,4-triazole (MSNT) (0.415 g, 1.4 mmol) followed by the addition of choline p-toluenesulfonate or 3-hydroxypropyltrimethylammonium p-toluenesulfonate (1.2 mmol) and the mixture was stirred at rt for 24 h. After cooling, the mixture was hydrolyzed by the addition of 2-propanol/$H_2O$, 7:2, and stirred for 0.5 h at rt. The solvents were evaporated in vacuo and the residue was subjected to flash column chromatography ($CH_2Cl_2$/MeOH/25% $NH_4OH$, 90:10:0.5 to 50:50:0.5) to afford the desired ether phospholipids.

General procedure (D) for the hydrogenation of ether phospholipids 16-20. To solution of phospholipids 11-15 (0.25 mmol) in MeOH (5 mL), Pd/C (10% w/w) was added and the resulting mixture was stirred under hydrogen atmosphere overnight. The mixture was filtered through a celite pad and the filtrate was evaporated under reduced pressure. The desired phospholipids 16-20 were obtained in pure form after flash column chromatography ($CH_2Cl_2$/MeOH/aq.$NH_3$, 80:20:1/50:50:1).

Example 1

5-cyclonentadecyloentyl
(2-(trimethylammonio)ethyl) phosohate (19)

5-cyclopentadecylidenepentanoic acid (6). Acid 6 was synthesized following the general procedure (A) above using cyclopentadecanone (2) and (4-carboxybutyl)triphenylphosphonium bromide, and was obtained as a colorless oil in 88% yield after purification by flash column chromatography (petroleum ether/EtOAc 95:5). $^1H$ NMR (300 MHz, $CD_3OD$) δ 11.22 (bs, 1H), 5.07 (t, J=6.72 Hz, 1H), 2.33 (t, J=7.33 Hz, 2H), 2.05-1.94 (m, 6H), 1.66 (q, J=7.94 Hz, 2H), 1.40-1.31 (m, 24H); $^{13}C$ NMR (75 MHz, $CDCl_3$) 179.3, 141.5, 123.8, 37.6, 33.8, 33.5, 33.2, 30.1, 29.0, 27.9, 27.7, 27.5, 27.3, 27.2, 26.9, 26.7, 26.6, 25.1, 24.5, 20.2.

5-(Cyclopentadecylidene)pentanol (10). Alcohol 10 was synthesized following the general procedure (B) above using acid 6 and was obtained as a colorless oil in 82% yield after flash column chromatography (PE/EtOAc 8:2). $^1H$ NMR (300 MHz, $CDCl_3$) δ 5.07 (t, J=6.71 Hz, 1H), 3.54 (t, J=6.11 Hz, 2H), 2.96 (bs, 1H), 2.01-1.90 (m, 6H), 1.52 (q, J=7.32 Hz, 2H), 1.32-1.28 (m, 26H); $^{13}C$ NMR (75 MHz, $CDCl_3$) δ 140.2, 124.7, 62.7, 37.5, 32.4, 29.9, 27.8, 27.6, 27.5, 27.4, 27.2, 26.8, 26.7, 26.2.

5-cyclopentadecylidenepentyl(2-(trimethylammonio) ethyl) phosphate (14). Compound 14 was prepared according to the general procedure (C) above using alcohol 10 and choline p-toluenesulfonate and was obtained as a gummy solid in 72% yield; $^1H$ NMR (300 MHz, $CD_3OD$) δ 5.03 (t, J=6.71 Hz, 1H), 4.19 (bs, 2H), 3.73 (bs, 4H), 3.26 (s, 9H), 1.93 (bs, 6H), 1.55-1.28 (m, 28H); $^{31}P$ NMR ($CD_3OD$) δ −1.07; $^{13}C$ NMR (75 MHz, $CD_3OD$) δ 140.3, 124.6, 66.2, 66.1, 65.7, 65.6, 59.2, 54.2, 37.6, 30.7, 29.9, 27.8, 27.7, 27.6, 27.4, 27.1, 26.7, 26.6, 26.5, 26.4.

5-cyclopentadecylpentyl (2-(trimethylammonio)ethyl) phosphate (19). Compound 19 was obtained following the general procedure (D) above using ether phospholipid 14, as a gummy solid (130 mg, 93%). $^1H$ NMR (300 MHz, $CD_3OD$) (δ) 4.20 (bs, 2H), 3.72 (bs, 4H), 3.29 (s, 9H), 1.53-1.22 (m, 37H); $^{31}P$ NMR (δ) −1.00; $^{13}C$ NMR (δ) 66.1, 65.8, 59.2, 54.2, 50.0, 44.9, 36.6, 35.3, 32.4, 31.0, 27.7, 27.2, 27.0, 26.8, 26.6, 26.5, 26.3, 24.6.

Comparative Example 1

4-cyclododecylidenebutyl (2-(trimethylammonio)ethyl) phosohate (11)

4-cyclododecylidenebutanoic acid (3). Acid 3 was synthesized following the general procedure (A) above using cyclododecanone (1) and (3-carboxypropyl) triphenylphosphonium, as a white solid in 31% yield after purification by flash column chromatography (Hex/EtOAc, 9:1). $^{1}$H-NMR (600 MHz, $CDCl_3$) δ: 5.18 (t, J=6.6 Hz, 1H), 2.40-2.36 (m, 2H), 2.07 (t, J=6.6 Hz, 2H), 2.02 (t, J=7.2 Hz, 2H), 1.55-1.50 (m, 2H), 1.44 (quintet, J=7.2 Hz, 2H), 1.36-1.25 (m, 16H); $^{13}$C NMR (150 MHz, $CDCl_3$) δ: 178.4, 139.7, 122.6, 34.4, 31.8, 28.8, 25.1, 24.9, 24.4, 24.3, 24.1, 24.0, 23.6, 23.4, 23.3, 12.4.

4-cyclododecylidenebutan-1-ol (7). Alcohol 7 was synthesized following the general procedure (A) above using acid 3 and was obtained as a yellowish solid in 77% yield after flash column chromatography (PE/EtOAc 90:10). $^{1}$H-NMR (600 MHz, $CDCl_3$) δ: 5.21 (t, J=7.2 Hz, 1H), 3.66 (t, J=6.6 Hz, 2H), 2.12 (q, J=7.2 Hz, 2H), 2.08-2.00 (m, 4H), 1.63 (quintet, J=6.6 Hz, 2H), 1.53 (quintet, J=6.6 Hz, 2H), 1.44 (quintet, J=6.6 Hz, 2H), 1.36-1.29 (m, 14H); $^{13}$C-NMR (150 MHz, $CDCl_3$) δ: 138.5, 124.5, 63.0, 33.2, 31.9, 28.6, 25.1, 24.8, 24.5, 24.41, 24.37, 24.18, 24.15, 24.0, 23.6, 23.3, 22.4.

4-cyclododecylidenebutyl (2-(trimethylammonio)ethyl) phosphate (11). Compound 11 was prepared according to the general procedure (C) above using alcohol 7 and choline p-toluenesulfonate as a viscous colorless oil in 64% yield; $^{1}$H-NMR (600 MHz, $CD_3OD$): δ 5.24 (t, J=6.6 Hz, 1H), 4.29-4.20 (m, 2H), 3.88 (q, J=7.2 Hz, 2H), 3.65-3.59 (m, 2H), 3.22 (s, 9H), 2.19-2.00 (m, 6H), 1.68 (quintet, J=6.6 Hz, 2H), 1.61-1.51 (m, 2H), 1.50-1.29 (m, 16H); $^{13}$C-NMR (150 MHz, $CD_3OD$): δ 139.2, 125.4, 67.5, 66.6 (d, $J_{cp}$=5.7 Hz), 60.3 (d, $J_{cp}$=5.0 Hz), 54.8, 54.6 (2C), 32.8, 32.4 (d, $J_{cp}$=7.4 Hz), 29.6, 26.1, 25.9, 25.3, 25.2, 25.0, 24.5, 24.3, 23.4; $^{31}$P-NMR ($CD_3OD$): δ −0.045; HRMS (ESI) (m/z): calcd. for $C_{21}H_{43}NO_4P$ $[M+H]^+$ 404.2930, found 404.2923; calcd. for $C_{21}H_{42}NNaO_4P$ $[M+Na]^+$ 426.2749, found 426.2742.

Comparative Example 2

5-cyclododecylidenenentyl (2-(trimethylammonio)ethyl) phosohate (12)

5-cyclododecylidenepentanoic acid (4). Acid 4 was synthesized following the general procedure (A) above using cyclododecanone (1) and (4-carboxybutyl)triphenylphosphonium bromide, as colorless oil in 81% yield (0.59 g) after purification by flash column chromatography (Hex/EtOAc, 9:1). $^{1}$H-NMR (300 MHz, $CDCl_3$): δ 5.17 (t, J=7.0 Hz, 1H), 2.36 (t, J=7.5 Hz, 2H), 2.13-2.00 (m, 6H), 1.75-1.19 (m, 21H); $^{13}$C-NMR (75 MHz, $CDCl_3$): δ 179.3, 141.5, 123.8, 37.6, 33.1, 30.1, 29.0, 27.9, 27.7, 27.5, 27.2, 26.8, 26.67, 26.63, 26.56, 25.1, 24.5.

5-cyclododecylidenepentan-1-ol (8). Alcohol 8 was synthesized following the general procedure (B) above using acid 4 and was obtained as a viscous oil in 99% yield after flash column chromatography (PE/EtOAc 8:2). $^{1}$H-NMR (300 MHz, $CDCl_3$) δ 5.17 (t, J=6.9 Hz, 1H), 3.60 (t, J=6.6 Hz, 2H), 2.11-1.90 (m, 6H), 1.68-1.16 (m, 23H); $^{13}$C-NMR (75 MHz, $CDCl_3$) δ 137.91, 125.01, 63.01, 32.59, 31.86, 28.63, 27.73, 26.36, 25.08, 24.82, 24.42, 24.36, 24.17, 24.12, 23.60, 23.27, 22.41.

5-cyclododecylidenepentyl (2-(trimethylammonio)ethyl) phosphate (12). Compound 12 was prepared according to the general procedure (C) above using alcohol 8 and choline p-toluenesulfonate and was obtained as a gummy solid in 72% yield; $^{1}$H-NMR (300 MHz, $CD_3OD$) δ 5.22 (t, J=7.0 Hz, 1H), 4.25 (d, J=2.4 Hz, 2H), 3.88 (q, J=6.5 Hz, 2H), 3.65-3.62 (m, 2H), 3.22 (s, 9H), 2.11-2.03 (m, 6H), 1.68-1.36 (m, 22H); $^{13}$C-NMR (75 MHz, $CD_3OD$) δ 138.74, 126.24, 66.91, 66.83, 60.29, 54.69, 32.72, 31.58, 29.60, 28.64, 27.47, 26.14, 25.88, 25.39, 25.33, 25.18, 25.04, 24.46, 24.27, 23.37; $^{31}$P-NMR ($CD_3OD$) δ −0.05; HRMS (ESI) (m/z): calcd. for $C_{22}H_{45}NO_4P$ $[M+H]^+$ 418.3086, found 418.3080; calcd. for $C_{22}H_{44}NNaO_4P$ $[M+Na]^+$ 440.2906, found 440.2896.

Comparative Example 3

5-cyclooentadecylideneoentyl (3-(trimethylammonio)propyl)phosohate (15)

5-cyclopentadecylidenepentyl (3-(trimethylammonio) propyl) phosphate (15). Compound 15 was prepared according to the general procedure (C) above using alcohol 10 and 3-hydroxypropyltrimethylammonium p-toluenesulfonate and was obtained as a gummy solid; yield 31%; $^{1}$H-NMR (300 MHz, $CDCl_3$): δ 5.07 (t, J=6.6 Hz, 1H), 4.00-3.88 (m, 2H), 3.78 (q, J=6.3 Hz, 2H), 3.72-3.62 (m, 2H), 3.27 (s, 9H), 2.15-2.05 (m, 2H), 2.03-1.91 (m, 6H), 1.64-1.51 (m, 2H), 1.42-1.25 (m, 26H); $^{13}$C-NMR (75 MHz, $CDCl_3$): δ 140.4, 124.8, 65.5 (d, $J_{CP}$=4.9 Hz), 64.2, 61.9 (d, $J_{CP}$=5.1 Hz), 53.4 (3C), 37.8, 30.9 (d, $J_{CP}$=7.1 Hz), 30.1, 28.0, 27.8, 27.79, 27.6, 27.3, 26.94, 26.87, 26.7, 26.6, 26.57, 24.8 (d, $J_{CP}$=4.9 Hz); $^{31}$P-NMR ($CDCl_3$): δ −0.26; HRMS (ESI) (m/z): calcd. for $C_{26}H_{53}NO_4P$ $[M+H]^+$ 474.3712, found 417.3703.

Comparative Example 4

4-cyclododecylbutyl (2-(trimethylammonio)ethyl) phosohate (16)

4-cyclododecylbutyl (2-(trimethylammonio)ethyl) phosphate (16). Compound 16 was prepared according to the general procedure (D) above using ether phospholipid 11, as a yellowish gummy solid in quantitative yield; $^{1}$H NMR (300 MHz, $CD_3OD$): δ 4.31-4.21 (m, 2H), 3.88 (q, J=6.3 Hz, 2H), 3.66-3.61 (m, 2H), 3.23 (s, 9H), 1.63 (quintet, J=6.6 Hz, 2H), 1.48-1.19 (m, 27H); $^{13}$C NMR (75 MHz, $CD_3OD$): δ 67.5, 66.9 (d, $J_{cp}$=5.8 Hz), 60.3 (d, $J_{cp}$=5.1 Hz), 54.7, 54.68, 54.63, 35.9, 35.2, 32.3 (d, $J_{cp}$=7.4 Hz), 30.2, 25.9, 25.2, 24.8, 24.5, 24.4, 22.8; $^{31}$P NMR (121 MHz, $CD_3OD$) δ −0.039; HRMS (ESI) (m/z): calcd. for $C_{21}H_4NNaO_4P$ $[M+Na]^+$ 428.2906, found 428.2895.

Comparative Example 5

5-cyclododecyloentyl (2-(trimethylammonio)ethyl) phosohate (17)

Compound 17 was obtained following the general procedure (D) above using ether phospholipid 12, as a yellowish gummy solid in quantitative yield; $^{1}$H NMR (300 MHz, $CD_3OD$) δ 4.25 (s, 2H), 3.87 (d, J=5.6 Hz, 2H), 3.63 (s, 1H), 3.22 (s, 9H), 1.64 (s, 2H), 1.36-1.24 (m, 30H), $^{13}$C NMR (75 MHz, $CD_3OD$): δ 67.48 (m), 66.9 (d, $J_{cp}$=5.9 Hz), 60.2 (d, $J_{cp}$=5.0 Hz), 54.74, 54.69, 54.64, 36.2, 35.2, 31.9 (d, $J_{cp}$=5.0 Hz), 30.2, 28.3, 27.3, 25.9, 25.2, 24.5, 24.4, 22.8; $^{31}$P NMR (121 MHz, $CD_3OD$) δ −0.04; HRMS (ESI) (m/z): calcd. for $C_{22}H_{45}NNaO_4P$ $[M+Na]^+$ 442.3062, found 442.3053.

Comparative Example 6

4-cyclonentadecylbutyl (2-(trimethylammonio)ethyl) phosphate (18)

4-cyclopentadecylidenebutanoic acid (5). Acid 5 was synthesized following the above general procedure (A) using cyclopentadecanone (2) and (3-carboxypropyl) triphenylphosphonium bromide, and was obtained as a colorless oil in 62% yield after purification by flash column chromatography (Hex/EtOAc, 9:1). $^1$H-NMR (300 MHz, $CDCl_3$) δ 5.10 (t, J=6.3 Hz, 1H), 2.41-2.28 (m, 4H), 2.04-1.95 (m, 2H), 1.36-1.21 (m, 27H); $^{13}$C NMR (75 MHz, $CDCl_3$) δ 179.54, 142.18, 122.49, 37.56, 34.67, 30.16, 27.92, 27.71, 27.43, 27.27, 26.92, 26.87, 26.71, 26.67, 26.65, 26.62, 26.59, 26.57, 23.33.

4-cyclopentadecylidenebutan-1-ol (9). Alcohol 9 was synthesized following the general procedure (B) above using acid 5 and was obtained as a viscous oil in 98% yield after flash column chromatography (PE/EtOAc 8:2). $^1$H NMR (300 MHz, $CDCl_3$) δ 5.14 (t, J=7.2 Hz, 1H), 3.64 (t, J=6.5 Hz, 2H), 2.12-1.95 (m, 6H), 1.66-1.56 (m, 2H), 1.44-1.20 (m, 25H) $^{13}$C NMR (75 MHz, $CDCl_3$) δ 141.04, 124.36, 62.99, 37.65, 33.18, 30.16, 27.96, 27.74, 27.54, 27.31, 26.93, 26.88, 26.71, 26.65, 26.62, 26.60, 26.57, 24.36.

4-cyclopentadecylidenebutyl (2-(trimethylammonio) ethyl) phosphate (13). Compound 13 was prepared according to the general procedure (C) above using alcohol 9 and choline p-toluenesulfonate and was obtained as a gummy solid in 78% yield; $^1$H-NMR (300 MHz, $CD_3OD$): δ 5.17 (t, J=7.2 Hz, 1H), 4.25 (d, J=2.4 Hz, 2H), 3.88 (q, J=6.6 Hz, 2H), 3.64-3.61 (m, 2H), 3.22 (s, 9H), 2.15-1.98 (m, 6H), 1.67 (dt, J=14.0, 6.8 Hz, 2H), 1.39-1.29 (m, 24H); $^{13}$C-NMR (75 MHz, $CD_3OD$): δ 141.7, 125.5, 67.5, 66.6, 60.3, 60.2, 54.7, 54.69, 54.64, 38.6, 32.5, 32.4, 31.0, 28.9, 28.7, 28.6, 28.4, 27.9, 27.9, 27.6, 27.59, 25.2; $^{31}$P-NMR ($CD_3OD$): δ −0.06; HRMS (ESI) (m/z): calcd. for $C_{24}H_{49}NO_4P$ $[M+H]^+$ 446.3399, found 418.3393; calcd. for $C_{24}H_{48}NNaO_4P$ $[M+Na]^+$ 468.3219, found 468.3204.

4-cyclopentadecylbutyl (2-(trimethylammonio)ethyl) phosphate (18). Compound 18 was obtained following the general procedure (D) above using ether phospholipid 13, as a gummy solid; yield quantitative (0.11 g); $^1$H-NMR (300 MHz, $CD_3OD$): δ 4.25 (s, 2H), 3.87 (q, J=6.5 Hz, 2H), 3.64-3.61 (m, 2H), 3.22 (s, 9H), 1.65-1.60 (m, 2H), 1.36-1.30 (m, 33H); $^{13}$C-NMR (75 MHz, $CD_3OD$): δ 66.1 (m), 65.5 (d, $J_{cp}$=5.9 Hz), 58.8 (d, $J_{cp}$=5.0 Hz), 53.35, 53.30, 53.2, 36.4, 34.7, 32.2, 30.9 (d, $J_{cp}$=5.0 Hz), 27.4, 26.7, 26.5, 26.4, 26.3, 24.4, 23.2; $^{31}$P-NMR (121 MHz, $CD_3OD$): δ −0.05; HRMS (ESI) (m/z): calcd. for $C_{24}H_{50}NNaO_4P$ $[M+Na]^+$ 470.3375, found 470.3365.

Comparative Example 7

5-cyclonentadecyloentyl (3-(trimethylammonio)propyl) phosohate (20)

Compound 20 was obtained following the general procedure (D) above using ether phospholipid 15, as a yellowish gummy solid; yield 96% (0.111 g); $^1$H-NMR (300 MHz, $CDCl_3$): δ 3.97-3.87 (m, 2H), 3.75 (q, J=6.5 Hz, 2H), 3.70-3.60 (m, 2H), 3.28 (s, 9H), 2.17-2.05 (m, 2H), 1.62-1.47 (m, 2H), 1.36-1.30 (m, 35H); $^{13}$C-NMR (75 MHz, $CDCl_3$): δ 65.6 (d, $J_{cp}$=6.4 Hz), 64.2, 61.8 (d, $J_{cp}$=5.9 Hz), 53.4 (3C), 36.8, 32.6, 31.3 (d, $J_{cp}$=7.7 Hz), 29.8, 27.9, 27.4, 27.2, 27.0, 26.8, 26.7, 26.6, 24.8; $^{31}$P-NMR (121 MHz, $CDCl_3$): δ −0.27; HRMS (ESI) (m/z): calcd. for $C_{26}H_{55}NO_4P$ $[M+H]^+$ 476.3869, found 476.3876.

Comparative Examples 8, 9

General Procedure (E) for the Homer-Emmons Reaction for the Synthesis of a,b-Unsaturated Esters 21 and 22

To an ice-cold suspension of NaH (60% dispersion in oil) (2.2 eq) in THF, triethyl phosphonoacetate (2.0 eq) was added dropwise. The resulting mixture was stirred at ambient temperature for 30 min, cooled at 0° C. and then a solution of the appropriate ketone (1 eq) in THF was added dropwise. The reaction mixture was stirred at room temperature overnight. Upon completion, the mixture was quenched with sat. $NaHCO_3$ and it was extracted thrice with EtOAc. The combined organic layers were dried over $Na_2SO_4$ and evaporated to dryness. Pure esters 21 and 22 were obtained after flash column chromatography.

General Procedure (F) for the Hydrogenation of a,b-Unsaturated Esters 23 and 24

To solution of a,b-unsaturated ester 21 or 22 (1 mmol) in EtOAc (20 mL), 10% Pd/C (10% w/w) was added and the resulting mixture was stirred under hydrogen atmosphere overnight. The mixture was filtered through a celite pad and the filtrate was evaporated under vacuo. The desired aliphatic esters 23 and 24 were obtained in pure form after flash column chromatography.

General Procedure (G) for the Reduction of Esters 25 and 26

To an ice-cold suspension of $LiAlH_4$ (2 eq) in THF (0.4 M), a solution of ester 23 or 24 (1 eq) in THF (0.2 M) was added dropwise. The resulting mixture was stirred at ambient temperature for 2 h. Subsequently, the reaction mixture was quenched at 0° C. by a mixture THF/$H_2O$ (1:1) and finally $H_2O$. $Na_2SO_4$ was added and the solids were filtered off, and the filtrate was diluted with EtOAc. The organic layers were washed twice with $H_2O$, dried over $Na_2SO_4$ and evaporated to dryness, to afford alcohols 25 and 26, respectively after flash column chromatography purification.

Comparative Example 8

2-cyclododecylethyl (2-(trimethylammonio)ethyl) phosohate (27)

Ethyl 2-cyclododecylideneacetate (21). a,b-unsaturated ester 21 was synthesized following the general procedure (E) above using cyclododecanone (1) (0.5 g, 2.74 mmol) and was obtained in the form of colorless oil in 80% yield (0.55 g) after purification by FCC (Hex/EtOAc, 98:2). $^1$H-NMR (600 MHz, $CDCl_3$): δ 5.73 (s, 1H), 4.13 (q, J=7.2 Hz, 2H), 2.71 (unresolved td, 2H), 2.20 (td, J=6.6 and 1.2 Hz, 2H), 1.64-1.59 (m, 2H), 1.58-1.51 (m, 2H), 1.44-1.24 (m, 14H), 1.27 (t, J=7.2 Hz, 3H); $^{13}$C-NMR (150 MHz, $CDCl_3$): δ 167.0, 163.1, 116.5 and 116.2 (E- and Z-), 59.6, 32.9, 29.9, 25.2, 25.0, 24.3, 24.1, 23.9, 23.6, 23.1, 22.3, 14.5; ESI-MS (m/z): 253.11 $[M+H]^+$.

Ethyl 2-cyclododecylacetate (23). Ester 23 was synthesized according to the procedure described (F) above in 92% yield (0.23 g) after purification by flash column chromatography (Hex/EtOAc, 98:2). $^{1}$H-NMR (600 MHz, $CDCl_3$): δ 4.22 (q, J=7.2 Hz, 2H), 2.19 (d, J=7.2 Hz, 2H), 2.01-1.96 (m, 1H), 1.41-1.27 (m, 22H), 1.24 (t, J=7.2 Hz, 3H); $^{13}$C-NMR (150 MHz, $CDCl_3$): δ 173.7, 60.2, 40.4, 31.6, 29.3, 24.6, 24.1, 23.6, 23.4, 21.8, 14.5; ESI-MS (m/z): 508.86 $[2M+H]^+$, 255.11 $[M+H]^+$.

2-cyclododecylethanol (25). Alcohol 25 was obtained according to the procedure (G) described above using ethyl 2-cyclododecylacetate (23) (0.2 g, 0.79 mmol) as a white solid in 87% yield (0.15 g) after flash column chromatography (Hex/EtOAc, 95:5). $^{1}$H-NMR (600 MHz, $CDCl_3$): δ 3.68 (t, J=6.6 Hz, 2H), 1.59-1.54 (m, 1H), 1.50 (q, J=6.6 Hz, 2H), 1.38-1.24 (m, 22H); $^{13}$C-NMR (150 MHz, $CDCl_3$): δ 61.6, 38.3, 30.9, 29.2, 25.0, 24.4, 23.47, 23.40, 21.8; ESI-MS (m/z): 213.19 [M+H].

2-cyclododecylethyl (2-(trimethylammonio)ethyl) phosphate (27). Compound 27 was prepared according to the general method (C) above using alcohol 25 (0.1 g, 0.47 mmol). Gummy solid; yield 78% (0.138 g); $^{1}$H-NMR (600 MHz, $CD_3OD$): δ 4.28-4.23 (m, 2H), 3.91 (q, J=7.2 Hz, 2H), 3.66-3.62 (m, 2H), 3.23 (s, 9H), 1.66-1.61 (m, 1H), 1.58 (m, 2H), 1.44-1.28 (m, 22H); $^{13}$C-NMR (150 MHz, $CD_3OD$): δ 67.4, 65.3 (d, $J_{CP}$=5.9 Hz), 60.2 (d, $J_{CP}$=5.0 Hz), 54.7, 54.67, 54.66, 37.1 (d, $J_{CP}$=7.2 Hz), 32.1, 30.0, 26.0, 25.4, 24.4, 24.3, 22.7; $^{31}$P-NMR ($CD_3OD$): δ −0.006; HRMS (ESI) (m/z): calcd. for $C_9H_{40}NNaO_4P$ $[M+Na]^+$ 400.2593, found 400.2583.

Comparative Example 9

2-cyclonentadecylethyl (2-(trimethylammonio)ethyl) phosohate (28)

Ethyl 2-cyclopentadecylideneacetate (22). a,b-unsaturated ester 22 was synthesized following the general procedure (E) above using cyclopentadecanone (2) (1.5 g, 6.68 mmol) and was obtained in the form of colorless oil in 94% yield (1.85 g) after purification by flash column chromatography (PE/EtOAc, 98:2). $^{1}$H-NMR (600 MHz, $CDCl_3$): δ 5.65 (s, 1H), 4.13 (q, J=7.2 Hz, 2H), 2.59 (unresolved td, 2H), 2.14 (unresolved td, 2H), 1.55-1.48 (m, 4H), 1.43-1.35 (m, 6H), 1.34-1.29 (m, 14H), 1.27 (t, J=7.2 Hz, 3H); $^{13}$C-NMR (150 MHz, $CDCl_3$): δ 166.7, 165.4, 115.8, 59.5, 38.8, 31.9, 28.0, 27.6, 27.2, 26.8, 26.79, 26.73, 26.68, 26.66, 26.64, 26.57, 26.50, 26.46, 14.5; ESI-MS (m/z): 295.37 $[M+H]^+$.

Ethyl 2-cyclopentadecylacetate (24). Ester 24 was synthesized according to the procedure (F) described above in 93% yield (0.28 g) after purification by flash column chromatography (PE/EtOAc 98/2). $^{1}$H-NMR (600 MHz, $CDCl_3$): δ 4.12 (q, J=7.2 Hz, 2H), 2.21 (d, J=7.2 Hz, 2H), 1.93-1.88 (m, 1H), 1.40-1.26 (m, 28H), 1.25 (t, J=7.2 Hz, 3H); $^{13}$C-NMR (150 MHz, $CDCl_3$): δ 173.7, 60.2, 40.5, 34.0, 32.5, 27.5, 27.1, 27.0, 26.8, 26.7, 24.6, 14.4; ESI-MS (m/z): 614.92 $[2M+Na]^+$, 297.19 $[M+H]^+$.

2-cyclopentadecylethanol (26). Alcohol 26 was obtained according to the procedure (G) described above using ethyl 2-cyclopentadecylacetate (24) (0.2 g, 0.68 mmol) as a colorless oil in 92% yield (0.16 g) after flash column chromatography (Hex/Acetone, 95:5). $^{1}$H-NMR (600 MHz, $CDCl_3$): δ 3.66 (t, J=7.2 Hz, 2H), 1.53-1.46 (m, 3H), 1.38-1.24 (m, 28H); $^{13}$C-NMR (150 MHz, $CDCl_3$): δ 61.5, 38.4, 33.3, 32.6, 27.7, 27.1, 26.9, 26.8, 26.7, 24.7; ESI-MS (m/z): 255.74 [M+H].

2-cyclopentadecylethyl (2-(trimethylammonio)ethyl) phosphate (28). Compound 28 was prepared according to the general procedure (C) above using alcohol 26 (0.1 g, 0.39 mmol). Gummy solid; yield 75% (0.123 g); $^{1}$H-NMR (300 MHz, $CD_3OD$): δ 4.58 (s, 1H), 4.29-4.21 (m, 2H), 3.91 (q, J=6.6 Hz, 2H), 3.65-3.60 (m, 2H), 3.22 (s, 9H), 1.63-1.54 (m, 2H), 1.43-1.27 (m, 28H); $^{13}$C-NMR (75 MHz, $CD_3OD$): δ 67.5, 65.3 (d, $J_{CP}$=5.9 Hz), 60.3 (d, $J_{CP}$=5.0 Hz), 54.7, 54.67 (2C), 37.2 (d, $J_{CP}$=7.2 Hz), 34.5, 33.5, 28.7, 28.1, 27.9, 27.8, 27.7, 25.7; $^{31}$P-NMR ($CD_3OD$): δ −0.009; HRMS (ESI) (m/z): calcd. for $C_{22}H_{47}NO_4P$ $[M+H]^+$ 420.3243, found 420.3235; calcd. for $C_{22}H_{46}NNaO_4P$ $[M+Na]^+$ 442.3062, found 442.3053.

Example 2

Large Scale Chemical Synthesis of 5-cyclonentadecyloentyl (2-(trimethylammonio)ethyl) phosohate (19)

The large scale synthesis of 5-cyclopentadecylpentyl (2-(trimethylammonio)ethyl) phosphate (19) involves four high yielding steps as shown below. The synthesis has been scaled up to 10 g batches.

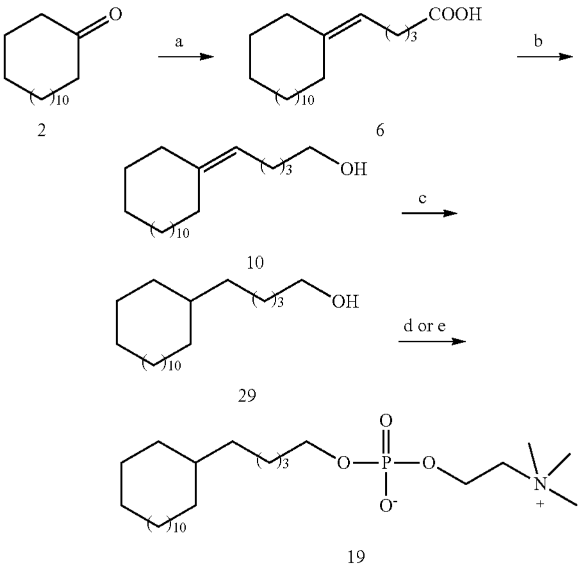

The above process describes the chemical synthesis of 5-cyclopentadecylpentyl (2-(trimethylammonio)ethyl) phosphate (19).

Reagents and conditions: (a) $HOOC(CH_2)_4Ph_3P^+Br^-$, tBuOK, THF, rt, overnight (88% yield); (b) $LiAlH_4$, THF, rt, 2 h (88% yield); (c) $H_2$, Pd/C, MeOH, overnight (92% yield); (d) (1) $POCl_3$, $Et_3N$, THF, −5° C., 15 min then $H_2O$, 30 min; (2) Pyridine, 45° C., 2.5 h; (3) Pyridine, choline p-toluenesulfonate, or choline tetraphenylborate, MSNT, 0° C. then rt, 24 h (55%); (e) (1) 1,2,4-triazole, $CHCl_3$, DIPEA, $POCl_3$ (2) DMAP, DIPEA or pyridine or $Et_3N$; (3) choline p-toluenesulfonate, or choline tetraphenylborate.

Experimental Procedures for the Multi-Pram Synthesis.

5-Cyclopentadecylidenepentanoic acid (6). To an ice-cold solution of (4-carboxybutyl)triphenylphosphonium bromide (19.75 g, 44.56 mmol) in THF (45 mL), potassium tert-butoxide (10.0 g, 89.12 mmol) was added and the mixture was stirred for 30 minutes at room temperature. Then a solution of cyclopentadecanone (2) (5.0 g, 22.28 mmol) in THF (11 mL) was added dropwise and the reaction was stirred at room temperature overnight. The solvent was removed in vacuo and the mixture was diluted with water and washed three times with $Et_2O$. The aqueous phase was then acidified to pH 2 and extracted with DCM, dried over $Na_2SO_4$ and evaporated to dryness. Pure acid was obtained as a colorless oil in 88% yield (6.09 g) after flash column chromatography (petroleum ether/EtOAc 95:5 to 90:10).

5-(Cyclopentadecylidene)pentanol (10). To an ice-cold suspension of $LiAlH_4$ (2.36 g, 62.24 mmol) in THF (75 mL), a solution of acid 6 (6.0 g, 19.45 mmol) in THF (80 mL) was added dropwise. The resulting mixture was stirred at ambient temperature for 2 h. Subsequently, the reaction mixture was quenched carefully at 0° C. by a mixture THF/$H_2O$ (1:1) and finally $H_2O$. $Na_2SO_4$ was added and the solids were filtered off and the filtrate evaporated. The residue was diluted with EtOAc, washed twice with $H_2O$, dried over $Na_2SO_4$ and evaporated to dryness to afford alcohol 10 as a colorless oil in 88% yield (5.04 g) which was used in the next step without further purification.

5-(Cyclopentadecyl)pentanol (29). To a solution of the unsaturated alcohol 10 (5.0 g, 16.98 mmol) in MeOH (400 mL), 10% Pd/C (0.5 g) was added and the resulting mixture was stirred under hydrogen atmosphere overnight. The mixture was filtered through a celite pad and the filtrate was evaporated under vacuo. The desired alcohol 29 was obtained as a colorless oil in 92% yield (4.63 g) after flash column chromatography (petroleum ether/EtOAc 95:5). $^1$H-NMR (600 MHz, $CDCl_3$): δ 3.64 (t, J=6.7 Hz, 2H), 1.64-1.07 (m, 37H); $^1$C-NMR (150 MHz, $CDCl_3$): δ 63.27, 36.58, 35.41, 33.01, 32.65, 27.82, 27.17, 26.96, 26.85, 26.71, 26.28, 24.85.

5-cyclopentadecylpentyl (2-(trimethylammonio)ethyl) phosphate (19). Procedure 1. To an ice-cold solution of $POC_3$ (2.26 mL, 24.29 mmol) in THF (310 mL) was added $Et_3N$ (4.67 mL, 33.4 mmol) followed by the dropwise addition of a solution of alcohol 29 (4.5 g, 15.18 mmol) in THF (350 mL). The mixture was stirred at ambient temperature for 2 h, and then $H_2O$ (400 mL) was added and stirring was continued for 1 h. The aqueous layer was extracted first with EtOAc and then with $CH_2Cl_2$. The combined organic extracts were dried over anhydrous $Na_2SO_4$ and the solvent was evaporated in vacuo to afford the corresponding phosphoric acid derivative, which was transformed to its corresponding pyridinium salt upon the addition of 220 mL of anhydrous pyridine and stirring for 2 h at 40° C. Then, the mixture was left to attain ambient temperature and the solvent was evaporated in vacuo. The oily residue was dissolved in dry pyridine and re-evaporated two more times. Finally, to an ice-cold solution of the pyridinium salt in dry pyridine (220 ml), choline p-toluenesulfonate (5.01 g, 18.22 mmol) or choline tetrafluoroborate was added followed by the portion wise addition of MSNT (6.3 g, 21.25 mmol). The mixture was stirred at rt for 24 h, cooled at 0° C., it was hydrolyzed by the addition of 2-propanol/$H_2O$, 7:2 (180 mL) and stirred for 1 h at rt. The solvents were evaporated in vacuo and the residue was subjected to flash column chromatography ($CH_2Cl_2$/MeOH/25% $NH_4OH$, 90:10:0.5 to 50:50:0.5) to afford the desired ether phospholipid 19 in 55% yield (3.85 g). The solvents were evaporated in vacuo and the residue was subjected to flash column chromatography ($CH_2Cl_2$/MeOH/25% $NH_4OH$, 90:10:0.5 to 50:50:0.5) to afford the desired ether phospholipid 94 in 55% yield (3.85 g).

5-cyclopentadecylpentyl (2-(trimethylammonio)ethyl) phosphate (19). Procedure 2. To a solution of 1,2,4-triazole (465.9 mg, 6.75 mmol) in anhydrous $CHCl_3$ (20 mL), anhydrous DIPEA (0.775 mL, 4.45 mmol) was added. Then, freshly distilled $POCl_3$ (0.189 mL, 2.02 mmol) was added to the mixture at 0° C. dropwise and the reaction mixture was stirred for 50 minutes at 0° C. Subsequently, DMAP (82.4 mg, 0.675 mmol) and DIPEA (0.4 mL, 2.3 mmol) were added followed by the dropwise addition of a solution of 5-cyclopentadecylpentan-1-ol (29) (400 mg, 1.35 mmol) in anhydrous $CHCl_3$ (9 mL) at 0° C. and the reaction mixture was stirred at 0° C. for 2h. Upon disappearance of the 5-cyclopentadecylpentan-1-ol (monitored by TLC) choline tosylate or choline tetraphenylborate (2.5 eq), was added at once and the mixture was stirred overnight at ° C. to room temperature. The reaction was quenched by the addition of a solution $H_2O$:i-PrOH 3:7.5 and pure product was obtained as white solid in 40% yield after FCC purification (DCM/MeOH, 10% $NH_4OH$ in MeOH, 9:1-7:3).

The advantages of using the large scale procedure of the above example over the prior art synthetic procedure are the higher purity and higher yield. The additional advantages of using procedure 2 over procedure 1 are that procedure 2 does not involve the use of pyridine which has a high boiling point and is difficult to remove, is a one pot reaction and doesn't require isolation of the intermediate phosphoric acid derivative.

Example 3

In Vitro Anti-Parasitic Activity and Toxicity

The in vitro antiparasitic activity against *L. infantum* (MHOM/MA/67/ITMAP-263) and the toxicity against THP-1 macrophages is presented in Table 1. Several compounds tested possess higher selectivity indices (SI) ranging from 7-fold to 11-fold compared to miltefosine.

TABLE 1

Anti-parasitic activity against *L. infantum* (MHOM/MA/67/ITMAP-263) intracellular amastigotes (infection with axenic amastigotes luciferase positive), cytotoxicity and selectivity index. Data from at least two independent determinations.

| | *L. Infantum* (MHOM/MA/67/ITMAP-263) | | | |
|---|---|---|---|---|
| Compound | Single Dose Assay 10 μM Mean Inhibitory Activity (%) ± SD | Dose Response Curves $IC_{50}$ ± SD (μM) | Toxicity $CC_{50}$ ± SD or NOAEL (μM) | Selectivity Index $CC_{50}/IC_{50}$ or NOAEL/$IC_{50}$ |
| Miltefosine | NT | 2.51 ± 1.73 | 15.9 ± 1.2 | 6.3 |
| 19 | 78 ± 2 | 1.4 ± 0.1 | >100 | >71 |
| 11 (Comparative Example 1) | 76 ± 22 | 2.59 ± 0.94 | >100 | >38.6 |

TABLE 1-continued

Anti-parasitic activity against *L. infantum* (MHOM/MA/67/ITMAP-263) intracellular amastigotes (infection with axenic amastigotes luciferase positive), cytotoxicity and selectivity index. Data from at least two independent determinations.

| | *L. Infantum* (MHOM/MA/67/ITMAP-263) | | | |
|---|---|---|---|---|
| Compound | Single Dose Assay 10 μM Mean Inhibitory Activity (%) ± SD | Dose Response Curves $IC_{50}$ ± SD (μM) | Toxicity $CC_{50}$ ± SD or NOAEL (μM) | Selectivity Index $CC_{50}/IC_{50}$ or NOAEL/$IC_{50}$ |
| 12 (Comparative Example 2) | 95 ± 2 | 0.9 ± 0.7 | >100 | >111 |
| 15 (Comparative Example 3) | 49 ± 1 | NT | >100 | ND |
| 16 (Comparative Example 4) | 87 ± 17 | 0.86 ± 0.33 | >100 | >116 |
| 17 (Comparative Example 5) | 96 ± 2 | 0.6 ± 0.2 | >100 | >166 |
| 18 (Comparative Example 6) | 97 ± 2 | 0.6 ± 0.3 | >100 | >166 |
| 20 (Comparative Example 7) | 53 ± 6 | NT | >100 | ND |
| 27 (Comparative Example 8) | 36 ± 5 | NT | >100 | ND |
| 28 (Comparative Example 9) | 70 ± 7 | 1.12 ± 0.45 | >100 | >90 |

NT: not tested (for $EC_{50}$ evaluation due to limited activity. If the activity at 10 μM (single dose) was inferior to 60% there was no interest in further pursuing this compound, and perform detailed studies for $EC_{50}$ determination).
ND: not determined (Selectivity index cannot be determined due to the absence of $EC_{50}$ value).

The anti-parasitic activity against *T. b. brucei* 1427 WT blood-stream form is presented in Table 2. The cyclopentadecylidene-substituted derivatives 17, 18 and 19 present unexpectedly high activity in the low micromolar range.

TABLE 2

Anti-parasitic activity against *T. b. brucei* L427 WT Blood-Stream Form (resazurin 72 h assay), cytotoxicity and selectivity index. Data from at least two independent determinations.

| | *T. b. brucei* L427 WT Blood-Stream Form | | | |
|---|---|---|---|---|
| Compounds | Single Dose Assay 10 μM Mean Inhibitory Activity (%) ± SD | Dose Response Curves $IC_{50}$ ± SD (μM) | Toxicity $CC_{50}$ ± SD or NOAEL (μM) | Selectivity Index $CC_{50}/IC_{50}$ or NOAEL/$IC_{50}$ |
| Miltefosine | NT | 33.9 ± 0.5 | 15.9 ± 1.2 | 0.47 |
| 19 | 99 ± 1 | 4.47 ± 0.2 | >100 | >22 |
| 11 (Comparative Example 1) | NA | NT | >100 | ND |
| 12 (Comparative Example 2) | 8 ± 8 | NT | >100 | ND |
| 15 (Comparative Example 3) | 14 ± 5 | NT | >100 | ND |
| 16 (Comparative Example 4) | NA | NT | >100 | ND |
| 17 (Comparative Example 5) | 21 ± 15 | NT | >100 | ND |
| 18 (Comparative Example 6) | 91 ± 12 | 7.44 ± 0.65 | >100 | >13 |

TABLE 2-continued

Anti-parasitic activity against *T. b. brucei* L427 WT Blood-Stream Form (resazurin 72 h assay), cytotoxicity and selectivity index. Data from at least two independent determinations.

| | *T. b. brucei* L427 WT Blood-Stream Form | | | |
|---|---|---|---|---|
| Compounds | Single Dose Assay 10 μM Mean Inhibitory Activity (%) ± SD | Dose Response Curves $IC_{50}$ ± SD (μM) | Toxicity $CC_{50}$ ± SD or NOAEL (μM) | Selectivity Index $CC_{50}/IC_{50}$ or NOAEL/$IC_{50}$ |
| 20 (Comparative Example 8) | 24 ± 10 | NT | >100 | ND |

NT: not tested (as in Table 1);
NA: not active (no activity was observed at 10 μM (single dose);
ND: not determined (as in Table 1).

The in vitro antiparasitic activity of compound 5-cyclopentadecylpentyl (2-(trimethylammonio)ethyl) phosphate (19) against *L. infantum* (2 species), *L. amazonensis, L. donovani* and *L. major* is presented in Table 3, as well as the toxicity against the human monocytic cell Line THP1 and PMA-differentiated THP-1 cells. The general higher potency of compound 19 over miltefosine is evident for the tested *Leishmania* species.

TABLE 3

Anti-leishmanial activity, cytotoxicity and selectivity index for 5-cyclopentadecylpentyl (2-(trimethylammonio)ethyl) phosphate (19). Data from at least two independent determinations.

| In vitro parameter determined | Compound 19 | Miltefosine |
|---|---|---|
| *L. infantum* intracellular amastigotes LEM235 $IC_{50}$ ± SEM (μM) | 0.7 ± 0.4 | 6.7 ± 1 |
| Cytotoxicity-Human Monocytic Cell Line THP1 $CC_{50}$ ± SD (μM) | >500 | 28.60 ± 2.48 |
| Selectivity[a] Index $CC_{50}/IC_{50}$ | 714 | 4.2 |
| L. infantum intracellular amastigotes (MHOM/MA/67/ITMAP-263) $IC_{50}$ ± SEM (μM) | 1.4 ± 0.1 | 3.2 ± 1.4 |
| Toxicity[b] $CC_{50}$ ± SD (μM) | >100 | 15.9 ± 1.2 |
| Selectivity Index[c,] $CC_{50}/IC_{50}$ or NOAEL/$IC_{50}$ | >71 | 5 |
| *L. donovani* 1SR intracellular amastigotes $IC_{50}$ ± SEM (μM) | 24 ± 3.8 | 12.67 ± 3.3 |
| *L. amazonensis* intracellular amastigotes $IC_{50}$ (μM) | 5.4 | 14.2 |

TABLE 3-continued

Anti-leishmanial activity, cytotoxicity and selectivity index for 5-cyclopentadecylpentyl (2-(trimethylammonio)ethyl) phosphate (19). Data from at least two independent determinations.

| In vitro parameter determined | Compound 19 | Miltefosine |
|---|---|---|
| *L. major* SASKH intracellular amastigotes $IC_{50}$ ± SEM (μM) | 15.5 ± 1.5 | 43.68 ± 8.34 |

SEM = standard error of mean;
SD = standard deviation.
[a]Selectivity Index (Cytotoxicity against Human Monocytic Cell Line THP1 $CC_{50}/IC_{50}$ *L. infantum* LEM235);
[b]MTT assay in PMA-differentiated THP-1 cells;
[c,]Selectivity Index (Cytotoxicity against PMA-differentiated THP-1 cells $CC_{50}/IC_{50}$ *L. infantum* MHOM/MA/67/ITMAP-263);
NOAEL = No Observed Adverse Effect Level (MTT assay in PMA-differentiated THP-1 cells).

Example 4

Cell-Based Toxicology (Early Toxicological Assessment)

The early toxicity properties against major CYP enzymes, hERG, Aurora B kinase, A549, THP-1 and W1-38 cell lines and mitochondrial toxicity are reported in Tables 4a and 4b. The absence of in vitro toxicity for compound 19 is clearly demonstrated. Conversely, compounds 12, 17, 18, 28 exhibit mitochondrial toxicity (Table 4b), while compounds 17 and 18 interact with CYP2C19, CYP2136 and CYP3A4 (Table 4a) which will influence their in vivo efficacy. Despite the good in vitro activity of compounds 12, 17, 18 and 28 against *L. infantum* (Table 1) they show liabilities with respect to the early toxicity assessment (ADMET profile).

TABLE 4a

Early toxicity properties in vitro (hERG, CYP1A2, CYP2C9, CYP2C19, CYP2D6). Compounds were tested at 10 μM. Values are reported as mean ± SD.

| Compound | % inhibition CYP1A2 | % inhibition CYP2C9 | % inhibition CYP2C19 | % inhibition CYP2D6 | % inhibition CYP3A4 |
|---|---|---|---|---|---|
| Miltefosine | −20.62 ± 11.85 | −0.8 ± 38.32 | 7.92 ± 15.50 | 30.83 ± 16.70 | 8.39 ± 8.99 |
| 19 | −32.10 ± 9.30 | −17.47 ± 2.31 | −18.16 ± 7.01 | −50.66 ± 3.45 | 17.65 ± 8.89 |
| 12 (Comparative Example 2) | 10.15 ± 5.03 | 1.76 ± 1.59 | 11.21 ± 5.40 | 15.11 ± 2.98 | 35.66 ± 6.01 |
| 15 (Comparative Example 3) | 9.44 ± 2.84 | 15.57 ± 6.17 | 41.99 ± 7.27 | 32.42 ± 2.88 | 23.42 ± 1.94 |
| 17 (Comparative Example 5) | 18.90 ± 0.69 | 10.35 ± 6.30 | 35.85 ± 4.97 | 48.86 ± 2.97 | 55.33 ± 4.28 |
| 18 (Comparative Example 6) | 14.00 ± 1.17 | 5.66 ± 5.52 | 33.33 ± 4.67 | 64.52 ± 2.92 | 38.12 ± 2.67 |

TABLE 4a-continued

Early toxicity properties in vitro (hERG, CYP1A2, CYP2C9, CYP2C19, CYP2D6). Compounds were tested at 10 μM. Values are reported as mean ± SD.

| Compound | % inhibition CYP1A2 | % inhibition CYP2C9 | % inhibition CYP2C19 | % inhibition CYP2D6 | % inhibition CYP3A4 |
|---|---|---|---|---|---|
| 20 (Comparative Example 7) | 10.14 ± 3.87 | 15.44 ± 0.53 | 52.28 ± 5.17 | 44.01 ± 3.51 | 22.83 ± 5.05 |
| 27 (Comparative Example 8) | 22.23 ± 1.59 | 13.66 ± 6.52 | 11.02 ± 5.72 | 6.92 ± 4.21 | 24.79 ± 3.15 |
| 28 (Comparative Example 9) | 15.55 ± 2.12 | 9.60 ± 4.60 | 21.30 ± 3.70 | 37.73 ± 3.27 | 27.78 ± 1.95 |

TABLE 4b

Early toxicity properties in vitro (hERG, A549, W1-38, mitochondrial toxicity, THP-1 cytotoxicities). Compounds were tested at 10 μM concentration unless otherwise specified. Values are reported as mean + SD.

| Compound | % inhibition hERG (Flag for Interference, hERG) | % cell growth A549* | % cell growth W1-38 | % mitochondrial toxicity** | Cytotoxicity THP-1 ($IC_{50}$) |
|---|---|---|---|---|---|
| Miltefosine | −16.92 ± 7.34 (no) | 95.8 ± 15.78 (at 1 μM) | 113.5 ± 26.66 (at 1 μM) | 3.39 ± 8.95 (at 1 μM) | 15.9 ± 1.2 |
| 19 | 4.06 ± 2.07 (no) | 108.28 ± 0.09 | 95.66 ± 19.68 | −3.22 ± 5.44 | >100 |
| 12 (Comparative Example 2) | −2.04 ± 7.61 (no) | 130.21 ± 5.63 | NT | 113.57 ± 12.08 | >100 |
| 15 (Comparative Example 3) | 15.47 ± 4.66 (no) | 112.20 ± 6.11 | 124.02 ± 7.42 | 1.08 ± 12.57 | >100 |
| 17 (Comparative Example 5) | 26.29 ± 12.93 (no) | 121.61 ± 8.94 | NT | 110.46 ± 13.08 | >100 |
| 18 (Comparative Example 6) | 34.84 ± 14.04 (no) | 132.80 ± 8.98 | NT | 109.49 ± 9.62 | >100 |
| 20 (Comparative Example 7) | 4.56 ± 15.55 (no) | 104.50 ± 4.67 | 98.77 ± 10.61 | −3.82 ± 5.49 | >100 |
| 27 (Comparative Example 8) | −4.11 ± 10.43 (no) | 126.46 ± 6.12 | NT | 113.87 ± 2.81 | >100 |
| 28 (Comparative Example 9) | 39.03 ± 5.84 (no) | 120.79 ± 0.63 | NT | 119.09 ± 14.82 | >100 |

NT: not tested (the compound was not tested for this property)
*100% Cell Growth = not Cytotoxic; 0% Cell Growth = Cytostatic; −100% Cell Growth = Cytotoxic.
**Mitochondrial Toxicity: 100% Mitotoxic; 0% not Mitotoxic.

As can be seen in Tables 4a and 4b the early toxicity properties of compound 19 in relation to the comparative examples differ, with 19 being non toxic in all screens. Therefore, it is evident that in vitro activity does not correlate with in vitro toxicities since for example compounds 17 and 18 with high activity against *L. infantum* amastigotes (c.f. Table 1) show significant inhibition of CYP2C19 and CYP21D6 at 10 μM (c.f. Table 4a).

In particular, the in vitro toxicity of 5-cyclopentadecylpentyl (2-(trimethylammonio)ethyl) phosphate (19) (10 μM) against hERG channel, cytochromes CYP1A2, CYP2C9, CYP2C19, CYP21D6, CYP3A4, cancer cell lines, mitochondria and Aurora B kinase is summarised in Table 5. Miltefosine was evaluated at 10 μM except for evaluation of the toxicity against A549, W1-38 cells and mitochondrial toxicity for which a 1 μM concentration was employed. Furthermore, compound 5-cyclopentadecylpentyl (2-(trimethylammonio)ethyl) phosphate (19) tested at 100 μM concentration does not inhibit the activity of HDAC4, HDAC9 and HDAC6, while an observed effect on HDACr is not considered significant. Miltefosine was tested at 10 μM (10 fold lower concentration) and also did not inhibit the activity of HDAC4, HDAC9, HDAC6 and HDAC8 (data not shown).

TABLE 5

In vitro evaluation of toxicities (hERG, CYP1A2, CYP2C9, CYP2C19, CYP2D6, CYP3A4 and A549 and WI38 cytotoxicities) of compound 19 (10 μM) and miltefosine (10 μM) or (1 μM for A549, W1-38, Aurora B kinase and mitochondrial toxicity). Values are presented as mean ± SD.

| In vitro toxicity | 5-cyclopentadecylpentyl (2-(trimethylammonio)ethyl) phosphate (19) | Miltefosine |
|---|---|---|
| Toxicity MTT assay in PMA-differentiated THP-1 cells (μM) | >100 | 15.9 ± 1.2 |
| Avg % inhibition hERG | 4.06 ± 2.07 (10 μM) | −16.92 ± 7.34 (10 μM) |
| Avg % inhibition CYP1A2 | −32.10 ± 9.30 (10 μM) | −20.62 ± 11.85 (10 μM) |
| Avg % inhibition CYP2C9 | −17.47 ± 2.31 (10 μM) | −0.80 ± 38.33 (10 μM) |
| Avg % inhibition CYP2C19 | −18.16 ± 7.01 (10 μM) | 7.92 ± 15.50 (10 μM) |
| Avg % inhibition CYP2D6 | −50.66 ± 3.45 (10 μM) | 30.83 ± 16.70 (10 μM)- |
| Avg % inhibition CYP3A4 | −17.65 ± 8.89 (10 μM) | 8.39 ± 8.99 (10 μM) |
| Avg % Cell growth A549 | 108.28 ± 0.09 (10 μM) | 95.80 ± 15.78 (10 μM) |
| Avg % Cell growth W1-38 | 95.66 ± 19.68 (10 μM) | 113.50 ± 26.66 (10 μM) |
| Ang % Toxicity Mitochondria | −3.22 ± 5.44 (10 μM) | 3.99 ± 8.95 (10 μM) |
| Avg % inhibition Aurora B | −9.92 ± 8.99 (10 μM) | −12.54 ± 0.71 (10 μM) |

Table 6 presents the in vitro hemolytic activity of compound 19 in comparison with miltefosine. The assay, which is an indicator of the toxic insult of a compound on the erythrocyte membrane is performed essentially as described in (Calogeropoulou T. et al., J. Med. Chem. 2008, 51, 897-908). The percentage of hemolytic activity of each drug at the specified concentration (100 μM) is approximately 11-fold lower for compound 19, signifying its much lower toxicity in this in vitro model.

TABLE 6

In vitro Hemolytic Activity in Human Erythrocytes

| Compound | Hemolysis, $HC_{50}$ (μM) | Hemolysis at 100 μM (%) |
|---|---|---|
| 19 | >100 | 8.7 |
| Miltefosine | 38.3 ± 2.8 | 96.1 |

Example 5

Physicochemical Properties of 5-Cyclonentadecyloentyl (2-(Trimethylammonio)Ethyl) phosohate (19)

The solubility of 5-cyclopentadecylpentyl (2-(trimethylammonio)ethyl) phosphate (19) was investigated in gastric fluids using nephelometry. More specifically, in Fasted and Fed State Simulated Intestinal Fluids (FASSIF and FESSIF) and in Simulated Gastric (stomach) Fluid (SGF). FASSIF, FESSIF and SGF are different types of biorelevant dissolution media that simulate the juices present in the human small intestine and stomach both before (fasted state) and after (fed state) eating food. The results are summarized in Table 7. Compound 19 exhibits similar solubility to miltefosine in simulated gastric fluids and slightly lower in PBS and water.

TABLE 7

Apparent solubilities of 5-cyclopentadecylpentyl (2-(trimethylammonio)ethyl) phosphate (19).

| Compound | Solubility in: FeSSIF (pH = 5) | FaSSIF (pH = 6.5) | SGF (pH = 1.6) | PBS (pH = 7.4) | $H_2O$ |
|---|---|---|---|---|---|
| 19 | >100 μM | >100 μM | 12.5 μM | <10 μM | <10 μM |
| Miltefosine | >100 μM | >100 μM | 12.5 μM | 25 μM | 25 μM |

As can be deduced from Table 7 compound 19 exhibits similar solubilities to miltefosine in all three simulated gastric fluids.

Furthermore, compound 19 is stable in human hepatic microsomes (samples were taken at 0, 5, 15, 30, 45 minutes) (Table 8), while the human plasma stability is 99.7% (samples were taken at 0, 15, 30, 45, 60, 120 minutes).

TABLE 8

Human microsomal stability and human plasma stability of 5-cyclopentadecylpentyl (2-(trimethylammonio)ethyl) phosphate (19).

| Compound | Human micro-somal Metabolic stability (%) | in vitro Intrinsic Clearance Clint (μL/min/ mg protein) | Degradation non NADPH dependent (%) | Human plasma Metabolic stability (%) |
|---|---|---|---|---|
| 19 | 100 | 0 | 0 | 99.7 |

Example 6

Ames Mutagenicity Testing

The test has been performed in duplicate as separate experiments (Table 9). Two different *Salmonella* strains were tested; TA98 (frameshift mutations) and TA100 (base pair substitutions, primarily at one of the GC pairs). Values above 15 represent genotoxicity. 5-cyclopentadecylpentyl) (2-(trimethylammonio)ethyl) phosphate (19) does not exhibit mutagenicity up to 100 μM.

TABLE 9

Evaluation of mutagenicity of 5-cyclopentadecylpentyl (2-(trimethylammonio)ethyl) phosphate 19 and miltefosine (concentration range 3.125-100 μM)

| TA98 | | TA100 | |
|---|---|---|---|
| Positive control | 48 ± 0 | Positive control | 46 ± 0 |
| Negative control | 7.33 ± 2.89 | Negative control | 13.33 ± 2.08 |
| Sterility control | 0 ± 0 | Sterility control | 0 ± 0 |
| 5-cyclopentadecylpentyl (2-(trimethylammonio)ethyl) phosphate (19) | | 5-cyclopentadecylpentyl (2-(trimethylammonio)ethyl) phosphate (19) | |
| 100 μM | 11.0 ± 1.41 | 100 μM | 8.5 ± 4.95 |
| 50 μM | 11 ± 2.82 | 50 μM | 10.0 ± 0 |
| 25 μM | 6.5 ± 3.53 | 25 μM | 7.0 ± 2.83 |
| 12.5 μM | 12.5 ± 4.95 | 12.5 μM | 14.0 ± 1.41 |
| 6.25 μM | 13.0 ± 2.83 | 6.25 μM | 9.0 ± 0 |
| 3.125 μM | 11.0 ± 8.48 | 3.125 μM | 7.5 ± 0.71 |

Example 7

Validation of 5-cyclopentadecylpentyl (2-(trimethylammonio)ethyl) phosohate (19) in vivo To validate the efficacy of 5-cyclopentadecylpentyl (2-(trimethylammonio)ethyl) phosphate (19) as an orally administered molecule against leishmaniasis a stepwise approach was followed including its pharmacology and toxicology and afterwards its efficacy against experimental infections by *L. infantum* in surrogate valid animal models (mice).

Pharmacology of 5-cyclopentadecylpentyl (2-(trimethylammonio)ethyl) phosphate (19) in mice. Pharmacokinetics of 5-cyclopentadecylpentyl (2-(trimethylammonio)ethyl) phosphate (19) was assessed, by snapshot PK, using BALB/c mice (n=2) after oral administration of 20 mg/kg determining its pharmacokinetic (PK) profile and associated parameters, namely tmax (time of reaching maximum concentration), Cmax (maximum concentration), Ke (elimination rate constant), t1/2 (plasma apparent half-life) and AUC (0-∞) (area under curve) in plasma. Blood samples were collected from the tail vein at 0, 0.5, 0.75, 1, 3, 24 and 72 hours into heparinized tubes. Moreover, biodistribution of the molecule, 72 h after administration, was determined in several organs of the treated mice, namely brain, liver, spleen, kidney, heart and bone marrow. For comparative purposes, similarly treated mice (NMRI, n=4) with miltefosine, were studied in parallel. Determinations of both miltefosine and 5-cyclopentadecylpentyl) (2-(trimethylammonio)ethyl) phosphate (19) were carried out using a modification (Jimenez-Antón M. D. et al., 2018. Eur J Pharm Sci. 121: 281-286) of the method described for miltefosine (Dorlo T. P. C. et al., 2008. J Chromatogr B, 865: 55-62) by liquid chromatography mass spectrometry (LC-MS/MS).

PK parameters showed that plasma concentration (Cmax) reached by 5-cyclopentadecylpentyl (2-(trimethylammonio) ethyl) phosphate (19) after oral gavage was comparatively lower and its half-life (t %) shorter than that observed for miltefosine (Table 10). However, the Cmax in plasma of 5-cyclopentadecylpentyl (2-(trimethylammonio)ethyl) phosphate (19) was 10-fold the $EC_{50}$ of the molecule for *L. infantum* in vitro. Given the superior antileishmanial (and antitrypanosomal) activity of 5-cyclopentadecylpentyl (2-(trimethylammonio)ethyl) phosphate (19) in vitro (see above), its shorter half-life constitutes a potential advantage of the new molecule.

TABLE 10

Mean and standard deviation of the pharmacokinetic parameters of miltefosine and 5-cyclopentadecylpentyl (2-(trimethylammonio)ethyl) phosphate (19) in healthy mice. BALB/c mice (6-8 weeks old) were gavaged with 20 mg/kg of 19. At defined time points (30, 45, 60, 180 minutes, 24, 48 and 72 hours) blood was collected from the tail and the compounds quantified.

| Parameters | Miltefosine | Compound 19 |
|---|---|---|
| tmax(h) | 24 | 24 |
| Cmax (μg/mL) | 30.6 ± 12.3 | 15.4 ± 9.3 |
| (μM) | (75.1 ± 30.2) | (33.4 ± 20.1) |
| Ke ($h^{-1}$) | 0.016 ± 0.002 | 0.049 |
| $t_{1/2}$ (h) | 43.3 ± 5.5 | 17.4 ± 4.2 |
| AUC (0-∞) (μg h/ml) | 2430 ± 972 | 966.8 ± 471.3 |
| (μM h/mL) | (5961 ± 2384) | (2094 ± 1020) |

The Ke for compound 19 is reported without standard deviation due to insufficient sample quantity.

The half-life of miltefosine was higher than that found for compound 19 suggesting its greater potential for persistence and bio-accumulation over time, which is believed to contribute to the development of resistance to miltefosine.

TABLE 11

Biodistribution of 5-cyclopentadecylpentyl (2-(trimethylammonio)ethyl) phosphate (19) and miltefosine in different tissues of mice 72 hours after the administration by oral gavage of 20 mg/kg of compound 19.

| | Treatment group | |
|---|---|---|
| Tissue | Miltefosine | Compound 19 |
| Plasma (μg/mL) | 14.1 ± 4.7 | 2.17 ± 0.55 |
| Brain (μg/g) | 1.5 ± 0.5 | 0.54 ± 0.61 |
| Liver (μg/g) | 15.5 ± 6.4 | 11.64 ± 0.88 |
| Spleen (μg/g) | 5.6 ± 2.6 | 2.31 ± 0.71 |
| Kidney (μg/g) | 38.7 ± 13.3 | 41.09 ± 15.79 |
| Heart (μg/g) | 6.2 ± 2.9 | 1.20 ± 0.90 |
| Bone marrow (μg/g) | 0.6 ± 0.1 | 0.20 ± 0.00 |

The biodistribution of compound 19 in different organs after 72 hours was evaluated (Table 11). When compared to the reference compound miltefosine, compound 19 presents 6.5 times less concentration in plasma than miltefosine. Interestingly this was not the case for the different organs evaluated. When we normalized the amount of compound 19 in organs for their relative abundance in plasma after 72 hours when compared to miltefosine it was evident that there is a bio-accumulation of compound 19 in the target organs (Table 12). Taken together these results suggest that 20 mg of compound 19 could be used in the in vivo efficacy validation as this quantity enables more than 10× the $EC_{50}$ in plasma and, apparently, no adverse effects in mice after the single dose administration. Therefore, we opted for the 20 mg/kg for the in vivo activity proof of principle in experimentally infected BALB/c mice.

TABLE 12

Average values of drug concentration ratio between tissues and plasma (tissue concentration/plasma concentration) for miltefosine and 5-cyclopentadecylpentyl (2-(trimethylammonio)ethyl) phosphate (19), 72 h after administration of 20 mg/kg by oral gavage.

| Tissue/Plasma ratio | Miltefosine | Compound 19 |
|---|---|---|
| Brain | 0.1 | 0.248 |
| Liver | 1.09 | 5.36 |
| Spleen | 0.39 | 1.06 |
| Kidney | 14.1 | 18.93 |
| Heart | 0.44 | 0.55 |
| Bone marrow | 0.04 | 0.09 |

Small structural difference in the claimed compounds may lead to undesirable pharmacokinetic characteristics. Table 13 below compares the pharmacokinetic characteristics of three closely related compounds, 17, 18 and 19.

TABLE 13

Mean and standard deviation of the the pharmacokinetic parameters of miltefosine and compounds 17, 18 and 19 in healthy mice. BALB/c mice (6-8 weeks old) were gavaged with 20 mg/kg of miltefosine, 17, 18 or 19. At defined time points (30, 45, 60, 180 minutes, 24, 48 and 72 hours) blood was collected from the tail and the compounds quantified.

| Parameters | Miltefosine | Compound 17 | Compound 18 | Compound 19 |
|---|---|---|---|---|
| tmax(h) | 24 | 3 | 5 | 24 |
| Cmax (μg/mL) | 30.6 ± 12.3 | 2.048 | 9.096 | 15.4 ± 9.3 |
| (μM) | (75.1 ± 30.2) | (4.88) | (20.32) | (33.4 ± 20.1) |
| Ke (h − 1) | 0.016 ± 0.002 | ND | ND | 0.049 |
| t½ (h) | 43.3 ± 5.5 | 6.9 | 16.3 | 17.4 ± 4.2 |
| AUC (0-∞) | 2430 ± 972 | 11.292 | 262.159 | 966.8 ± 471.3 |
| (μg h/ml) | (5961 ± 2384) | (26.91) | (585.65) | (2094 ± 1020) |
| (μM h/mL) | | | | |

ND = not determined,

The Cmax and $t_{1/2}$ values for compounds 17 and 18 are reported without standard deviation due to insufficient sample quantity.

The structure of compound 17 [5-cyclododecylpentyl (2-(trimethylammonio)ethyl) phosphate, comparative example 5] differs from that of compound 19 only in that it is substituted with a 12-member carbon ring instead of a 15-member ring. This compound is more potent in vitro against *Leishmania* compared to 19 (Table 1). Regarding the pharmacokinetics, 17 has a much shorter tmax (h), AUC and maximum concentration (Cmax). This makes it unsuitable for in vivo administration.

The structure of compound 18 [4-cyclopentadecylbutyl (2-(trimethylammonio)ethyl) phosphate, comparative example 6] differs from that of compound 19 only in that the carbon chain between the 15-member carbon ring and the phosphate group is 4 carbons long (instead of being 5 carbons long as in 19) and it is 2.3-fold more potent in vitro against *Leishmania* compared to 19 (Table 1). It has comparable pharmacokinetic characteristics to 19 (a shorter tmax (h) and around half the Cmax).

Therefore, based on the above analysis in vitro potency against *Leishmania* is not sufficient to predict pharmacokinetic characteristics.

Example 8

Maximum Tolerated Dose and Dose Range Finding Determination in Rodents

The primary objective of the dose range finding study is to establish the maximum tolerated dose (MTD) as determined by parameters such as clinical signs and reductions in body weight and food consumption, and to provide the data for appropriate dose selection in subsequent regulatory toxicology studies.

Seven groups of animals with 4 animals/group were treated daily by oral gavage with either compound 19 or miltefosine for 7 days. Preliminary studies support the use of 100 mg/kg as the maximum tolerated dose for a 7 day trial. Taking this into consideration, the 50 mg/kg dose was selected as an intermediate dose and 20 mg/kg as a non-toxic dose. The same doses were used for the reference drug miltefosine.

Figure 1B:
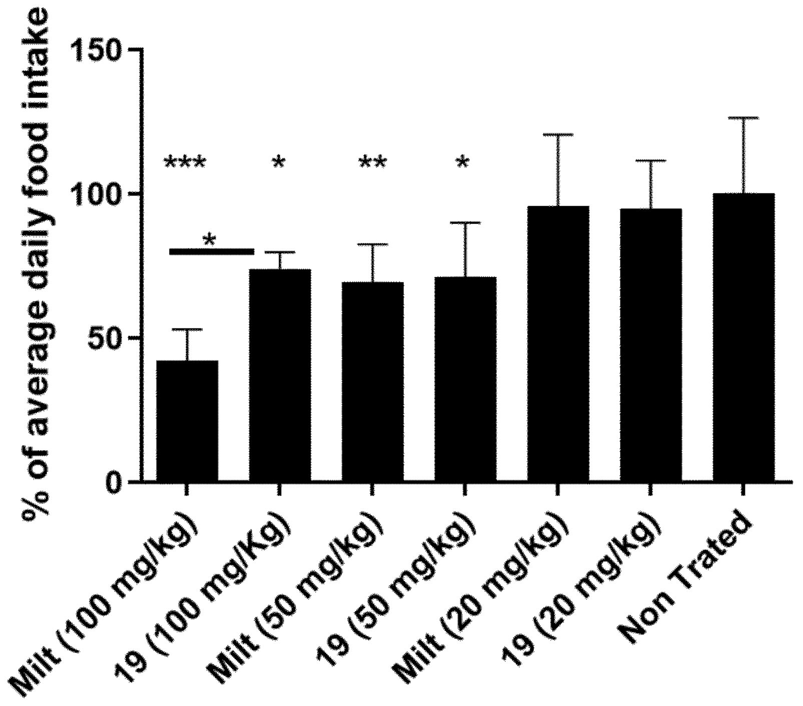

During the experiment the animals treated with 100 mg/kg of either compound presented a time dependent deterioration of the physical condition that was more severe for miltefosine (FIG. 1). The treatments with 100 and 50 mg/kg of both compounds significantly diminished the food uptake of the animals when compared to the controls (FIG. 1A). Moreover the treatment with 100 mg/kg of miltefosine induced also a significant lesser food intake when compared to the equivalent treatment of compound 19. The treatments with 100 mg/kg lead to a weight loss over the course of the experiment that was significant from day 4 onwards for miltefosine and day 5 for compound 19 (FIG. 1B). The average weight loss at the end of the experiment was 19±6% for miltefosine (upper limit based on ethics) and 11±4 for compound 19. For the 50 mg/kg treatments the weight loss was only significant for miltefosine at day 7. The pattern of weight loss for this amount of compounds is also noteworthy with almost 50% of the weight loss happening after the first treatment. Then the weight loss is very moderate over the remainder 6 treatments. The average weight loss at the end of the experiment was 11±3 and 7±8% for miltefosine and compound 19 respectively. The 20 mg/kg treatments did not result in any significant weight loss with the weight variation being indistinguishable from the controls.

The available hematological and biochemical data (not shown) are not suggestive of any major dose dependent physiological disturbance.

Ultimately the greater weight loss variation for the equivalent doses (100 and 50 mg/kg) and the significant lesser food intake associated with miltefosine at the 100 mg/kg treatment when compared to compound 19 demonstrates that miltefosine induced more disturbances to the animals than compound 19, suggesting it is less toxic than miltefosine.

FIG. 1 illustrates the changes in food intake and weight variation associated to the dose range finding study in rodents. (A) Average food intake (±SD) for the duration of the experiment, each point represents the registered daily food uptake. *$P<0.05$; $P<0.01$; *$P<0.001$ as determined by Bonferroni's Multiple Comparison Test for comparison with non-treated group. (B) Average weight loss (±SD) associated to the treatments for the duration of the experiment. *$P<0.05$; $P<0.01$; *$P<0.001$ as determined by Bonferroni's Multiple Comparison Test.

Example 9

Efficacy test of 5-cyclonentadecyloentyl (2-(trimethylammonio)ethyl) phosohate (19) in BALB/c Mice Experimentally Infected with *Leishmania infantum* (21-Day Treatment)

The effect of compound 19 on BALB/c mice experimentally infected with *Leishmania infantum* was evaluated at a dose of 2.5, 5, 10 or 20 mg/Kg/day administered by oral gavage for 21 days (FIG. 2).

Figure 2A:
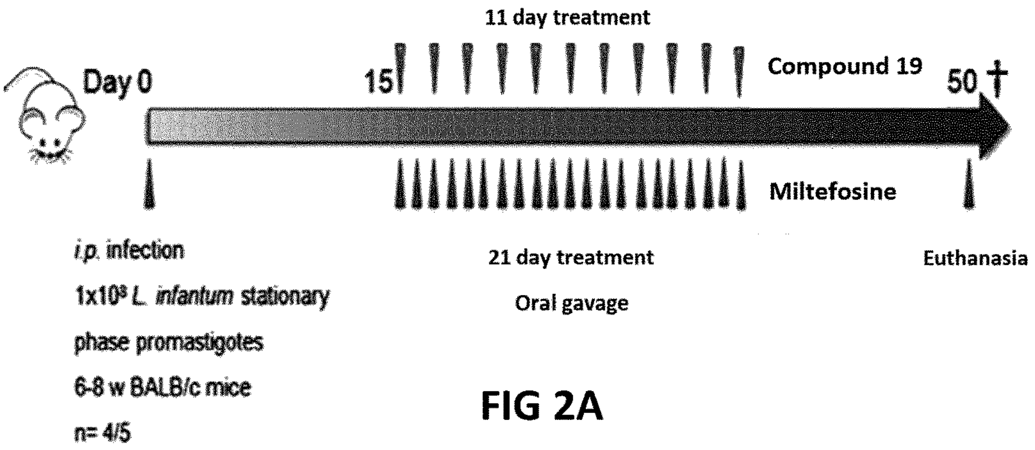
FIG. 2 illustrates the in vivo efficacy of 5-cyclopentadecylpentyl (2-(trimethylammonio)ethyl) phosphate (19) and miltefosine in *L. infantum*-infected mice, treated by oral gavage for 21 consecutive days with miltefosine and every other day for compound 19, with 20, 10, 5 and 2.5 mg/kg. (A) General infection and treatment scheme; (B) and (C) are graphic presentations of parasite burden in the spleen and the liver, respectively, evaluated by limiting dilution assay.
Figure 2B:
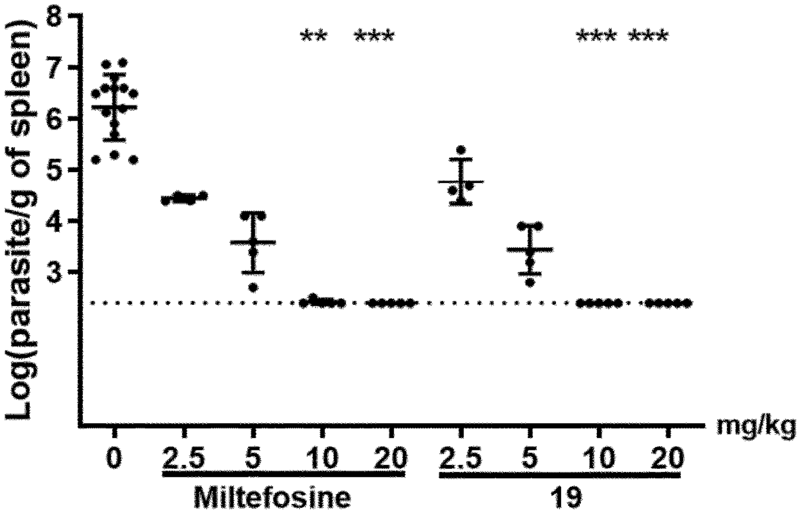

Taking in consideration that preliminary PK data suggested that the amount of compound 19 remains high after 48 hours (similar to 24 hours) and also that the compound shows high bio-accumulation in the kidneys, it was decided to use a treatment scheme of every other day. To better understand the potential of compound 19, four doses were selected, 20, 10, 5 and 2.5 mg/kg, and the animals were treated for 21 days (FIG. 2A). The rationale for the choice of four doses was to enable dose dependent information in activity and toxicity. The wait period of 15 days after treatment end enabled the follow up of reappearance of infection and also the determination of the time dependent compound elimination.

Figure 2C:
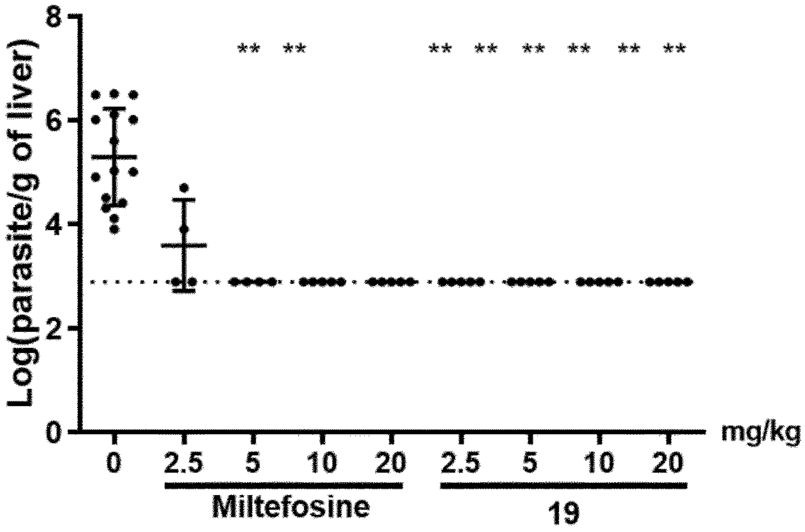

BALB/c mice (6-8 weeks old) were infected intraperitoneally with $1\times10^8$ stationary phase *L. infantum* promastigotes. Two weeks after infection, compound 19 or miltefosine were administered by oral gavage for 21 consecutive days (20 mg/kg or 10 mg/kg) for miltefosine and every other day for compound 19. Three days after the last treatment the mice were euthanized and parasite burden (log number of parasites/mg of organ) was evaluated by limiting dilution assay, essentially as described in Tavares. J. et al (Methods Mol Biol, 2019; 1971:289-301), in the spleen (FIG. 2B) and in the liver (FIG. 2C). Data represent the mean±SD, $*p<0.05$, $**p<0.01$ (One way ANOVA with Dunnett's test) in comparison with the untreated group.

As expected, miltefosine 20 mg/kg maintained parasite burden under the detection limit while at 10 mg/kg one of the animals presented detected parasites in the spleen (FIG. 2). For the lower doses miltefosine was not able to maintain the parasite burden under the detection limit although the parasite burden reduction was more than 99%. In the liver, only the treatment with 2.5 mg/kg did not result in parasite burdens under the detection limit (still reduction of 98%). For compound 19 the treatments maintained parasite burden under the detection limit for both organs with the exception of 2.5 mg/kg in the spleen that induced an average reduction of parasite burden of 98%.

Organ weight, hematological and biochemistry profile did not present significant differences between treated and not treated groups for the experiment with 20 mg/kg. The same was evident for 10 mg/kg and lower doses (data not shown).

Example 10

Efficacy Test of 5-cyclonentadecyloentyl (2-(trimethylammonio)ethyl) phosohate (19) in BALB/c Mice Experimentally Infected with *Leishmania infantum* (10-Day Treatment)

Figure 3A:
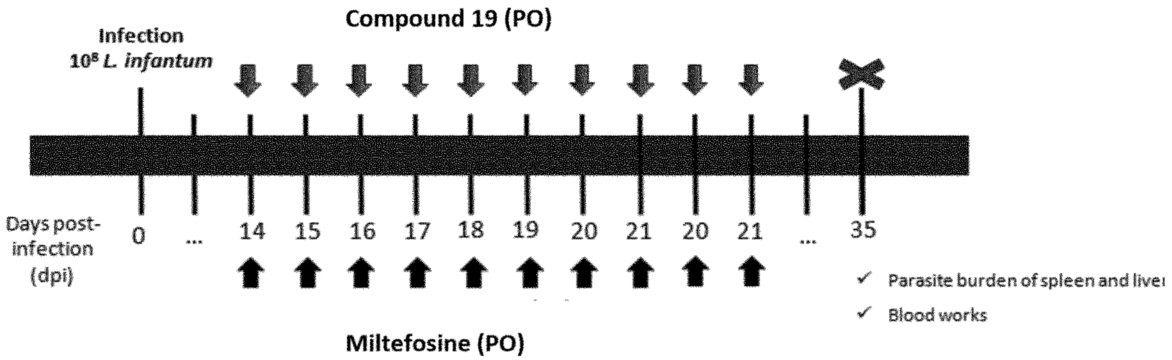
FIG. 3 shows in vivo efficacy results from a 10-day treatment in *L. infantum*-infected mice. (A) Experimental approach; (B) and (C) are graphic presentations of parasite burden in the spleen and the liver, respectively, evaluated by limiting dilution assay.

To further address compound 19 superiority over miltefosine, a shorter treatment scheme was utilized on BALB/c mice experimentally infected with *L. infantum* (FIG. 3). The treatments were reduced to 10 consecutive days at doses of 2.5, 5, 10 or 20 mg/Kg/day (FIG. 3).

Figure 3B:
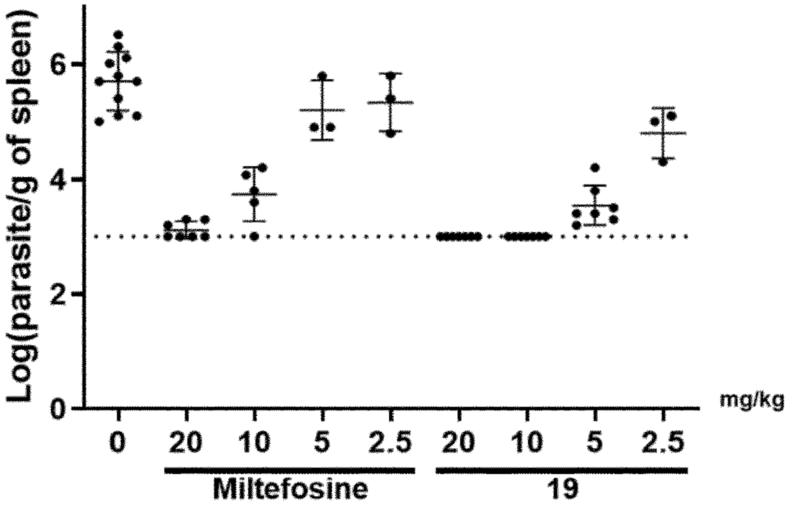
Figure 3C:
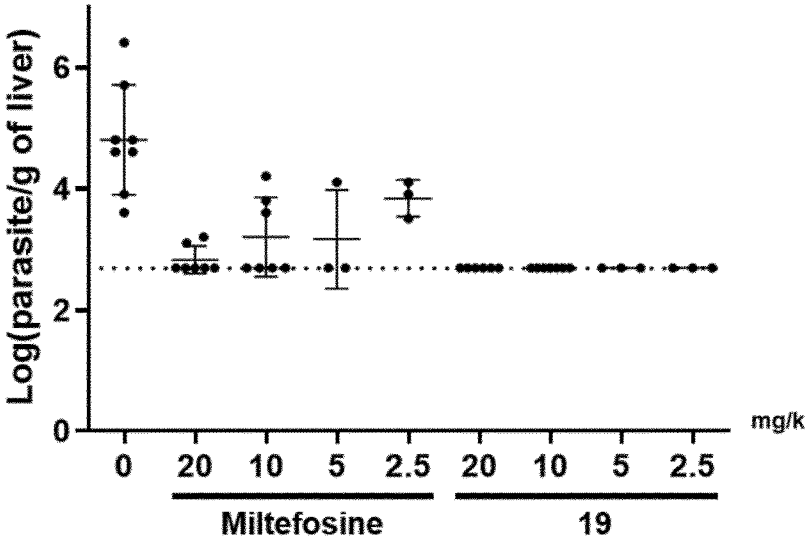

In the spleen the parasite burdens observed clearly show that the treatments with 20 mg/kg and 10 mg/kg compound 19 are able to maintain parasite burden below the detection limit. The 5 and 2.5 mg/kg treatments enabled reductions of parasite burden of 99±1 and 91±6% for spleen, respectively (FIG. 3B). For the liver all the compound 19 treatments maintained the parasite load under the detection limit. Miltefosine treatments with 20 and 10 mg/kg although highly effective (average reduction of parasite load >99%) were not able to maintain parasite burden under the detection limit. The treatments with 5 and 2.5 were less effective with average parasite burden reductions of 70±36 and 64±33%. In the liver miltefosine was able to reduce the average parasite burden by more than 98% for all tested concentrations (FIG. 3C). Therefore the data demonstrate that compound 19 is more effective at reducing parasite burden than miltefosine in both organs evaluated. These data support what was suggested for the longer treatment schemes and fully endorse the superiority of compound 19 over miltefosine in BALB/c infection model.

Example 11

Compound 18 (Comparative Example 6) Lacks in Vivo Efficacy Against *Leishmania*

Figure 4A:
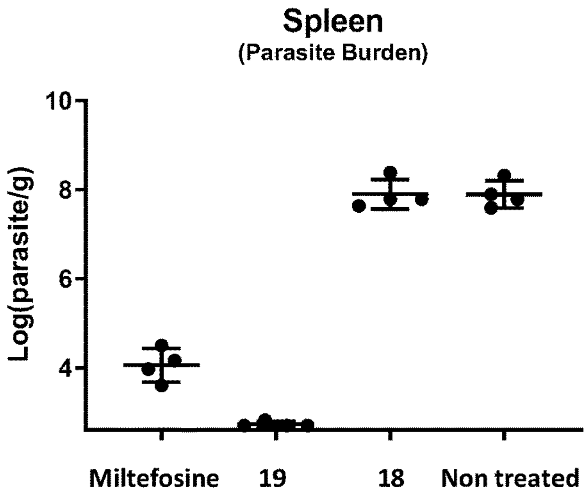
FIG. 4 illustrates the in vivo activity of compounds 18 and 19 in a model of infection with *L. infantum* axenic amastigotes expressing luciferase (10 consecutive treatments with 10 mg/kg of each compound, evaluated by limiting dilution assay 2 weeks after the last treatment).
Figure 4B:
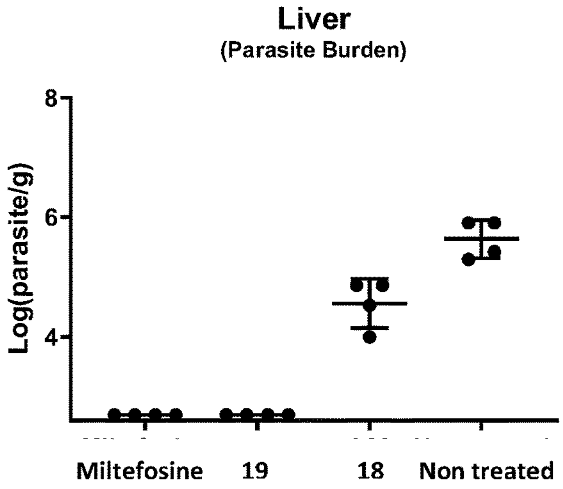
Figure 4C:

In vivo activity of compounds 18 and 19 (ten consecutive oral treatments with 10 mg/kg of each compound, followed by a break of 2 weeks after last treatment), was studied in a model of infection with axenic amastigotes expressing luciferase, essentially as described in (Mendes Costa D. et al, J. Sci Rep. 2019 Dec. 12; 9(1):18989; Tavares J. et al., Methods Mol Biol. 2019; 1971:289-301). (FIG. 4). Unlike miltefosine, compound 19 was able to reduce the parasites in the bone marrow, under the detection limit (FIG. 4C). Surprisingly, compound 18 was not effective in reducing the parasitic burden in the spleen, liver or bone marrow of the infected animals.

Example 12

Efficacy of 5-cyclonentadecyloentyl (2-(trimethylammonio)ethyl) phosohate (19) in HAT Mice Model Using *T. b. brucei*

Figure 5A:
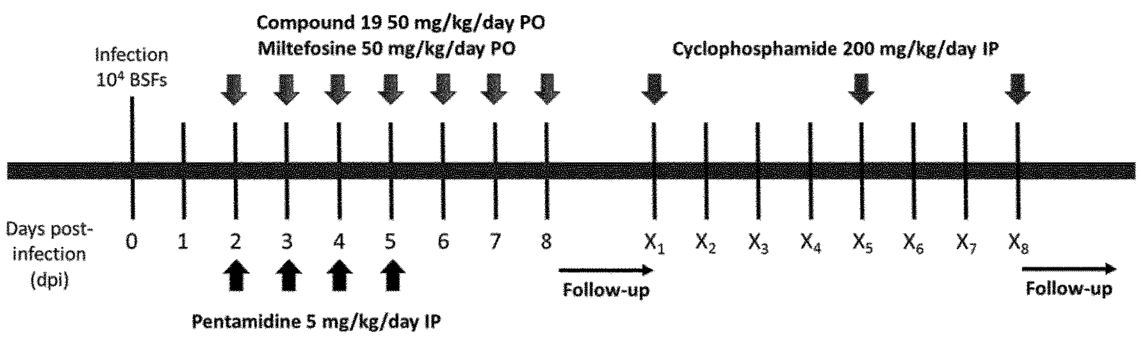
FIG. 5 shows the in vivo efficacy of 5-cyclopentadecylpentyl (2-(trimethylammonio)ethyl) phosphate (19) at 50 mg/kg/day in mice infected with T. b. *brucei*: (A) General infection and treatment scheme. (B) Overall evolution of parasite burden assessed by live imaging using IVIS Lumina LT (Perkin Elmer) during and after treatment. *T. b. brucei* Lister 427 expressing red-shifted luciferase was used in these experiments. DX is the day post treatment. (C) Quantification of bioluminescent signal plotted as average radiance (p/s/$cm^2$/sr) during and after treatment.
Figure 5B:
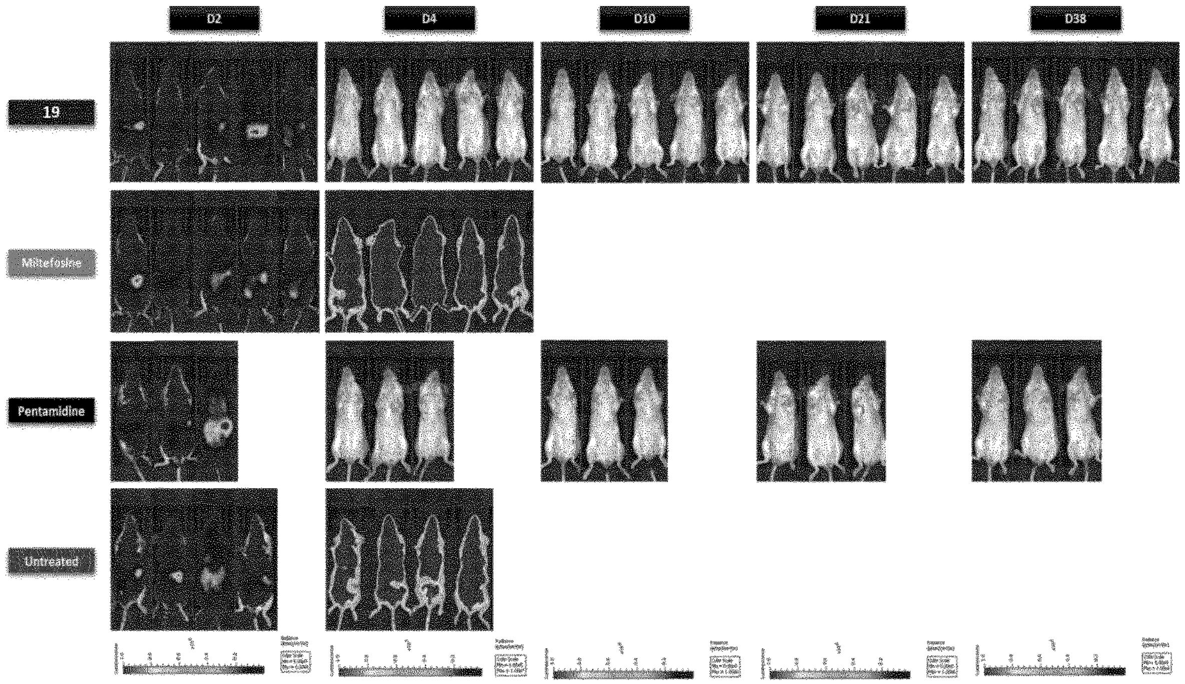
Figure 5C:
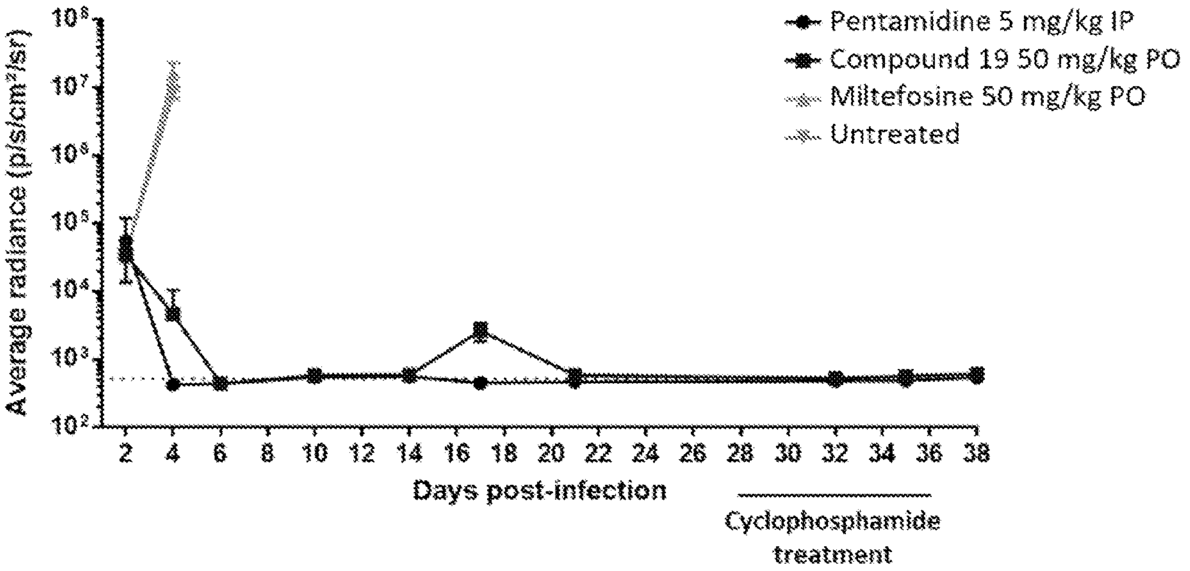
Figure 6A:
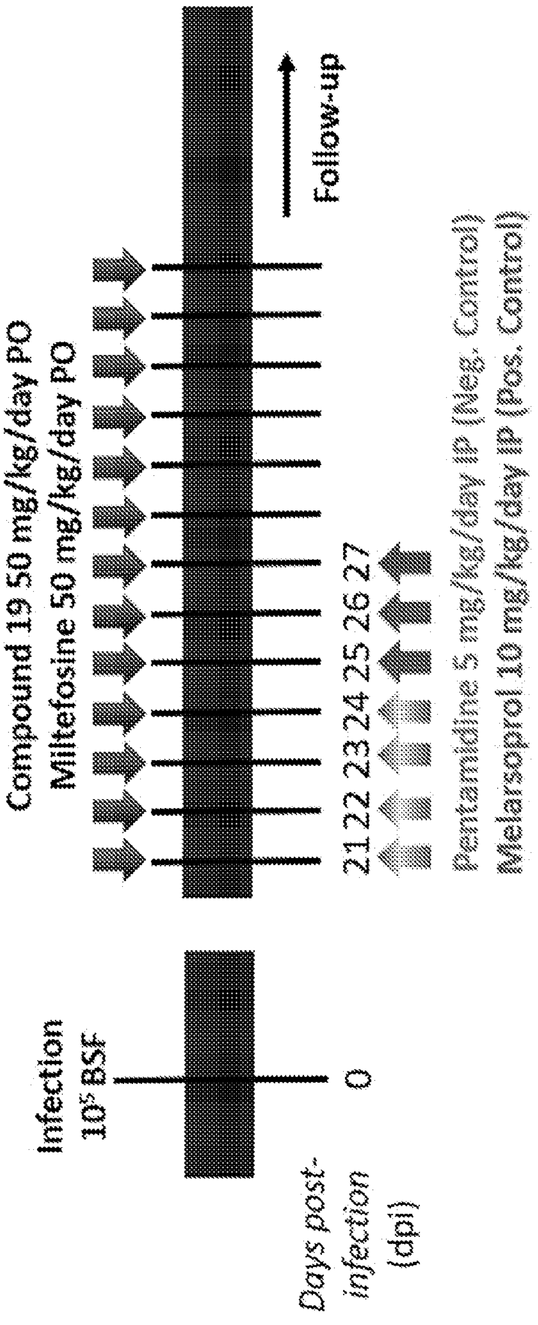
FIG. 6 shows the effects of 5-cyclopentadecylpentyl (2-(trimethylammonio)ethyl) phosphate (19) treatment in *T. brucei* infection stage II mice model. (A) Experimental setup for the preliminary treatment of *T. b. brucei* GVR35 infection with compound 19, miltefosine, pentamidine and melarsoprol. (B) Overall evolution of parasite burden assessed by live imaging using IVIS Lumina LT (Perkin Elmer) during and after treatment. *T. b. brucei* Lister 427 expressing red-shifted luciferase was used in these experiments. (C) Quantification of bioluminescent signal plotted as average radiance (p/s/cm2/sr) during and after treatment. (D) Quantification of bioluminescent signal, in a region in interest defined in the head, plotted as average radiance (p/s/cm2/sr) during and after treatment. (E) Quantification of ratio between the signal (as determined by the average radiance) in the region of interest defined in the head of the animals and the overall signal in the animal. (F) Contribution of the signal in the head (as determined by the average radiance) to the overall signal in the animal. (G) Weight (average±standard deviation) of animals for the treatment and post-treatment period. (H)—Individual animal weight for the treatment and post-treatment period. All statistical analysis was performed with graphpad software package using 1 way ANOVA Dunns multiple comparison test, $*P<0.05$; $P<0.01$; $*P<0.001$.
Figure 6B:
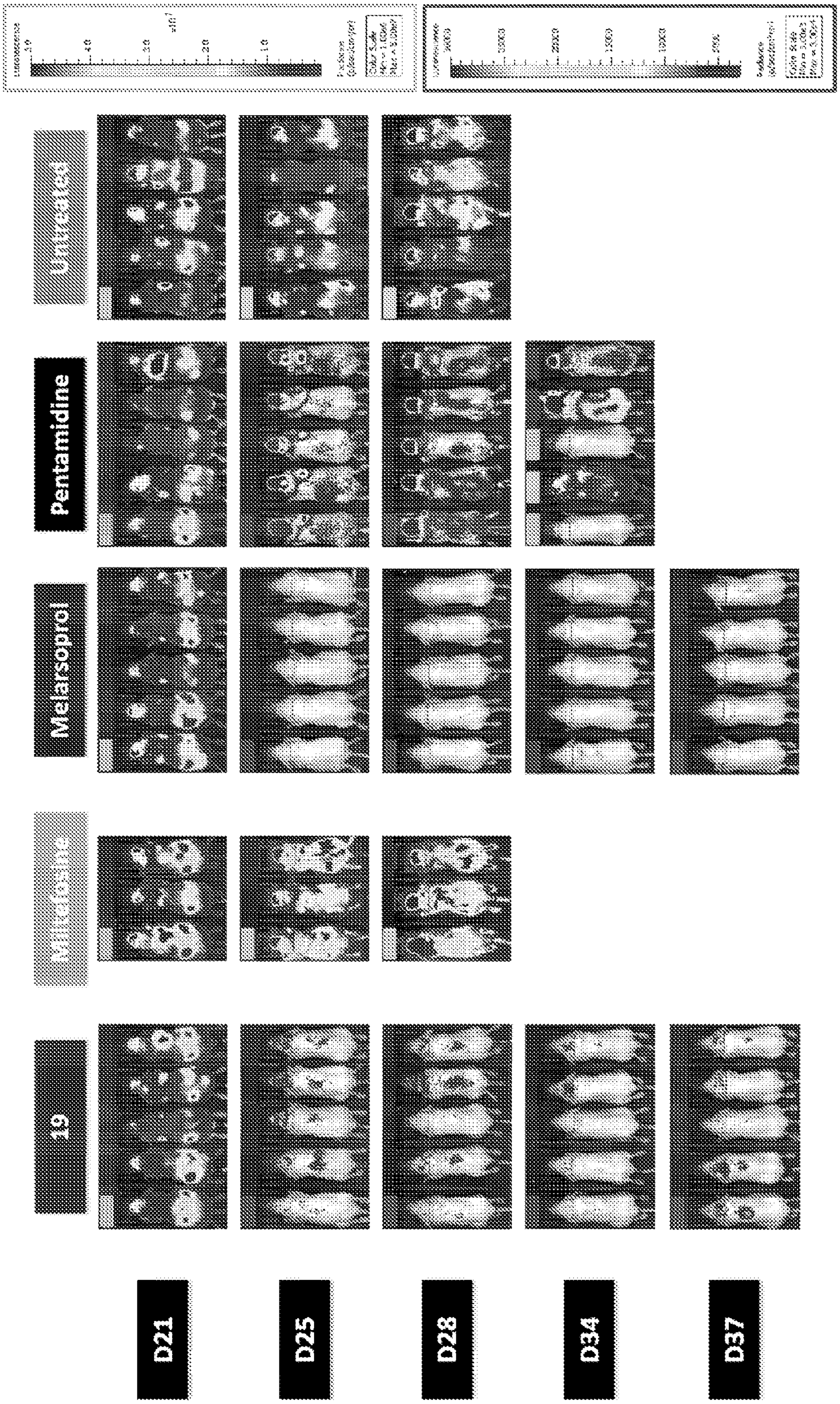
Figure 6C:
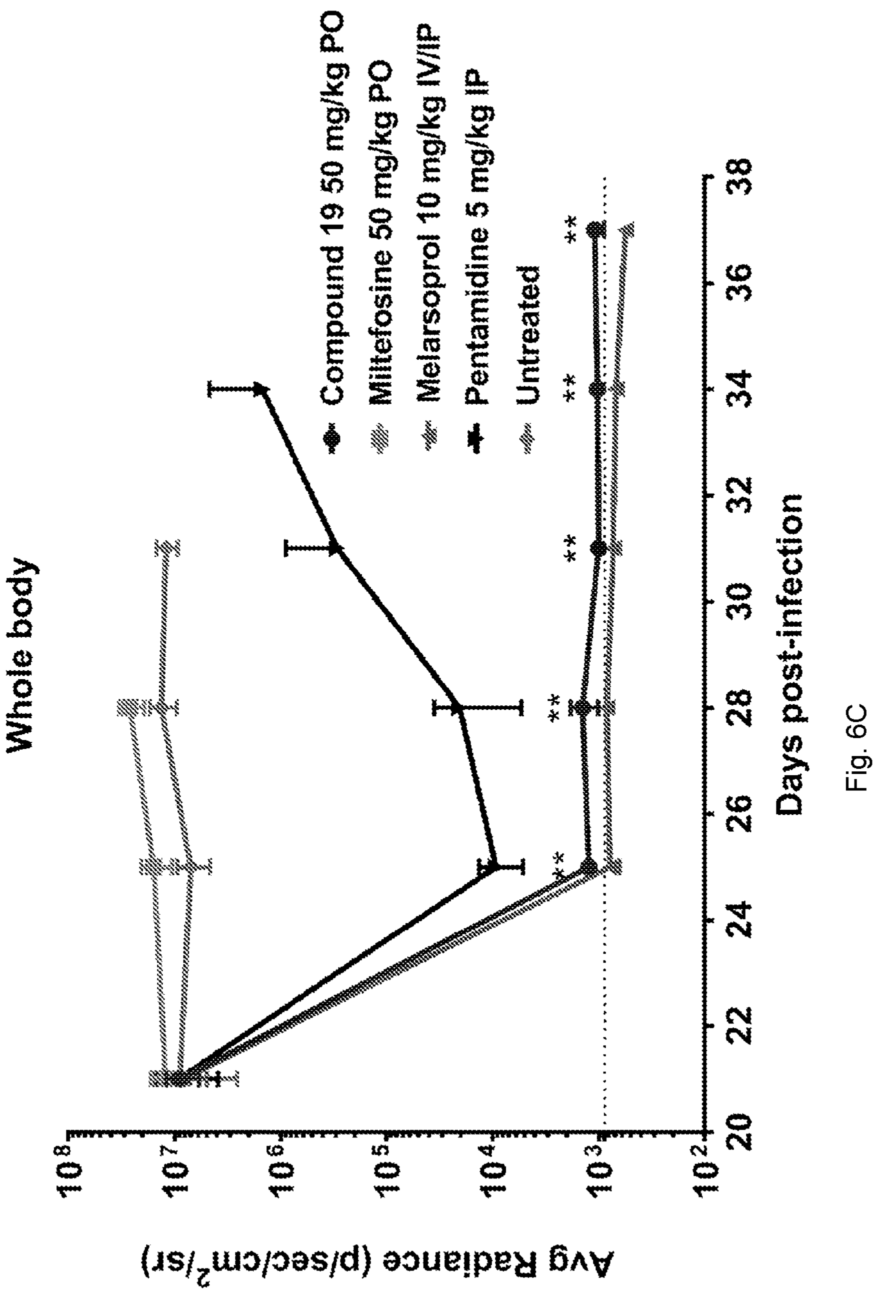
Figure 6D:
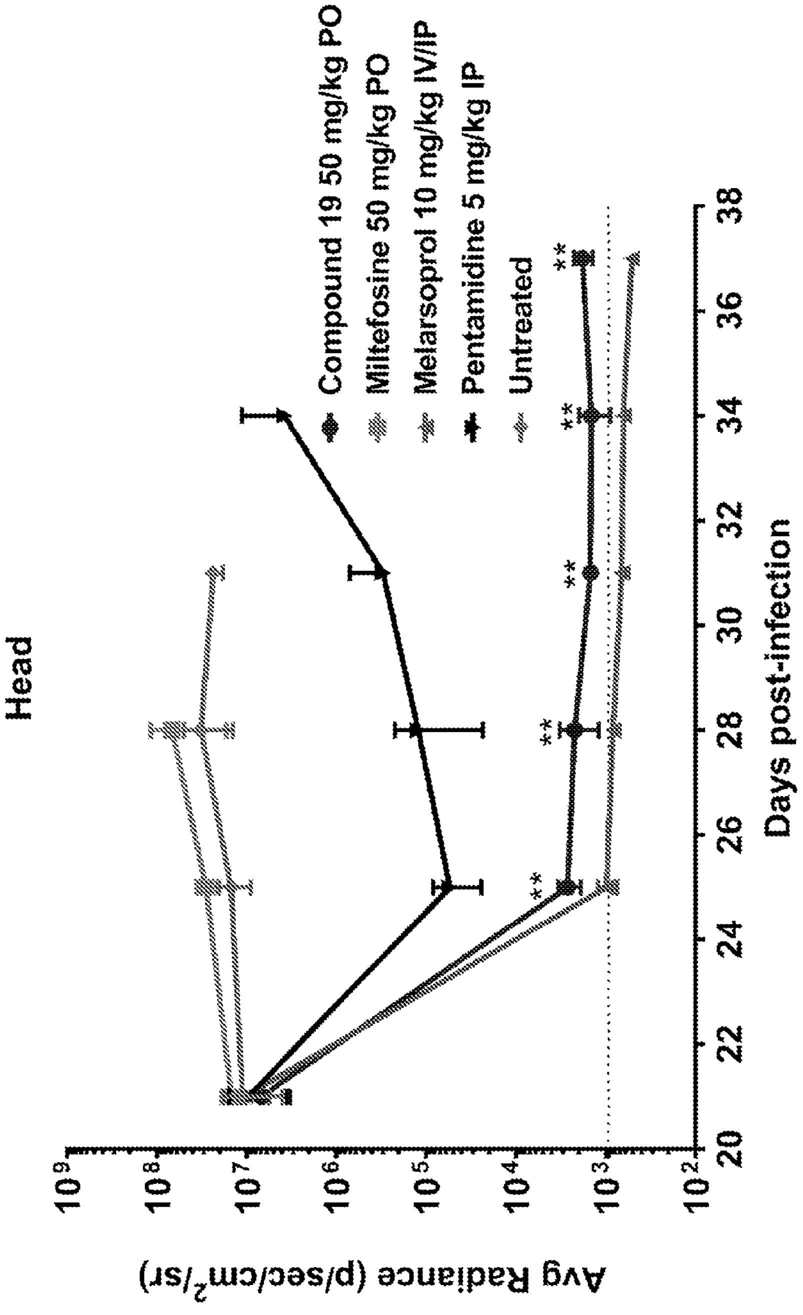
Figure 6E:
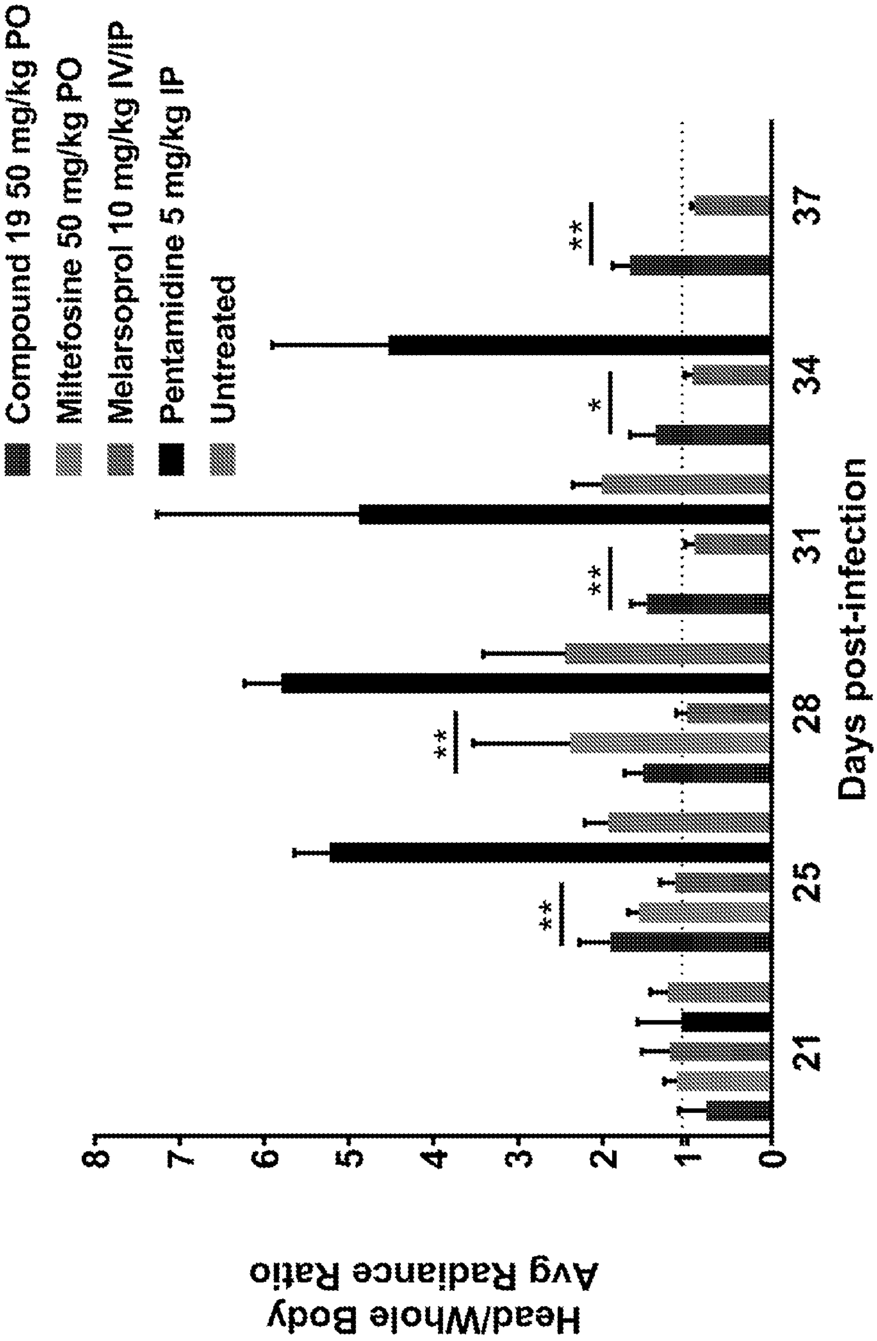
Figure 6F:
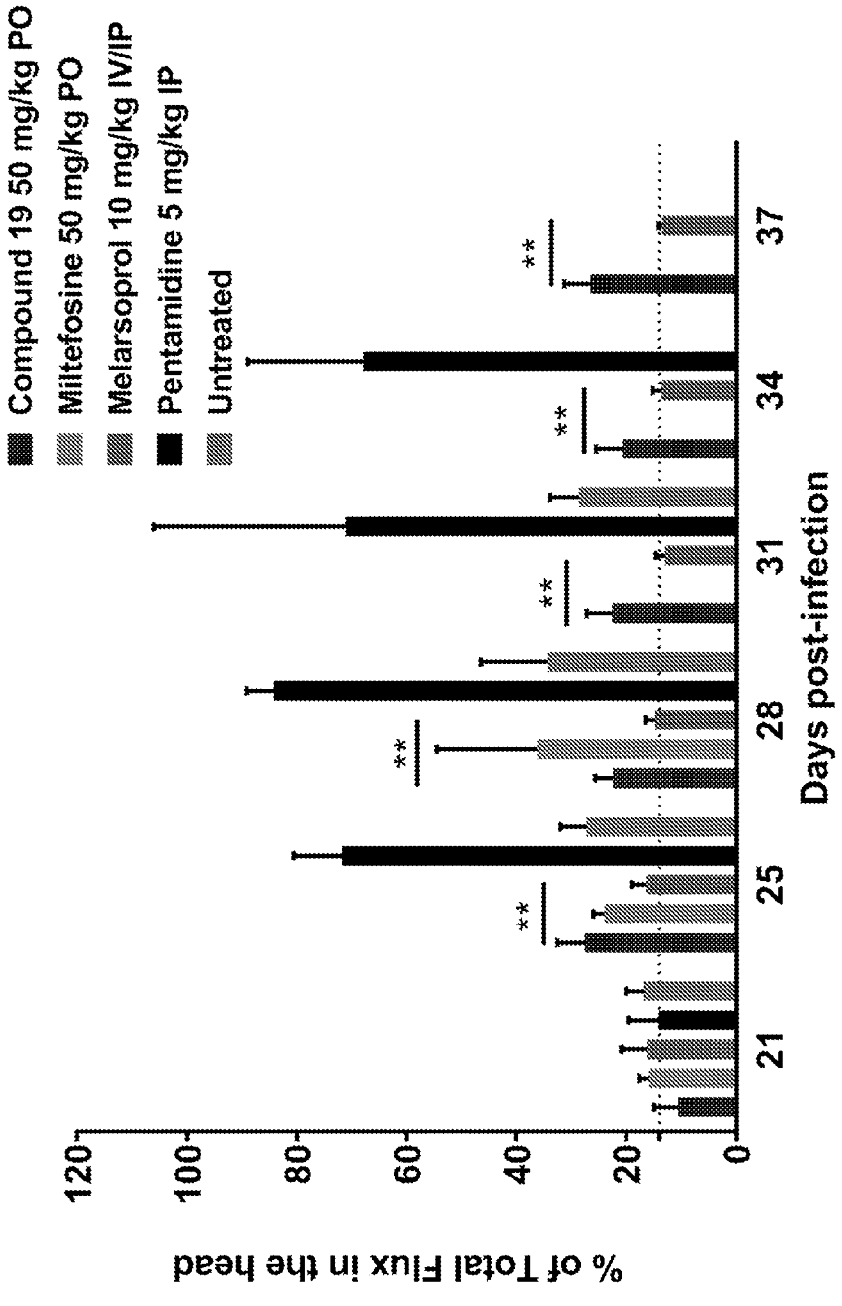
Figure 6G:
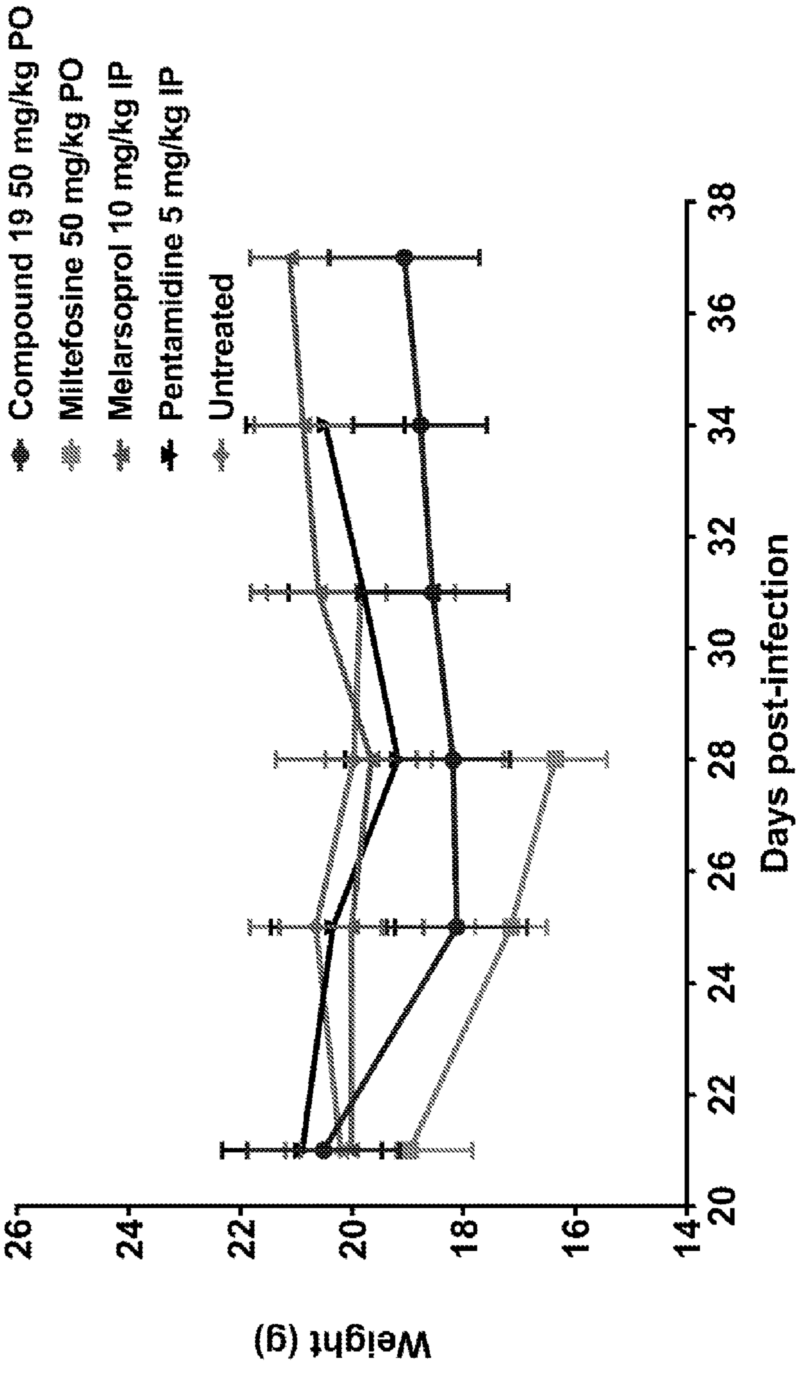
Figure 6H:
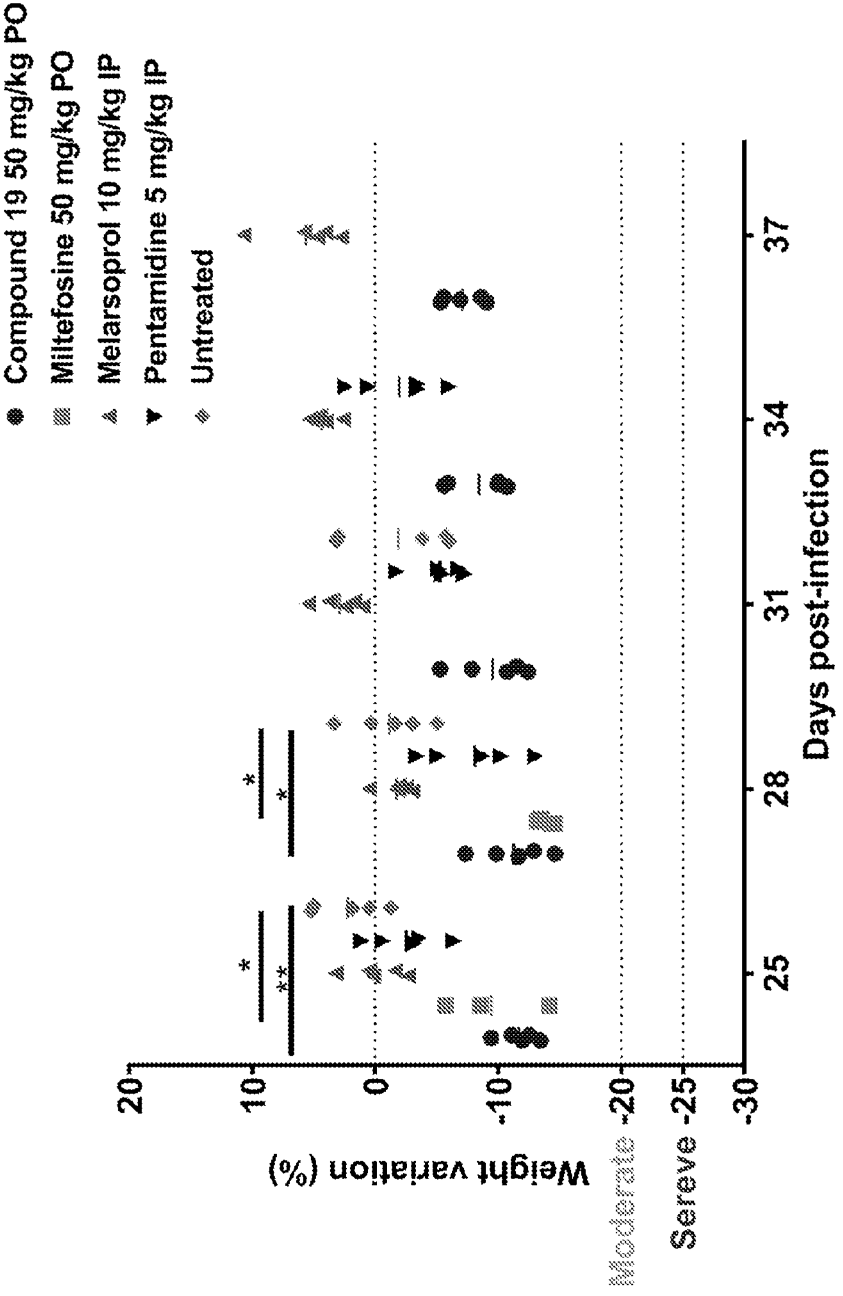

A 50 mg/kg/day of compound 19 seven-day PO treatment of BALB/c mice infected with *T. brucei brucei* eliminated the infection (FIG. 7).). *T. brucei brucei* Lister 427 expressing red-shifted luciferase was used in these experiments as described for *L. infantum* in vivo infection in (Graça N A et al., Antimicrob Agents Chemother. 2016 Mar. 25; 60(4): 2532-6). The overall evolution of parasite burden assessed by live imaging using IVIS Lumina LT (Perkin Elmer) during and after treatment. As a supplementary control, besides pentamidine, the inventors used miltefosine in an equivalent treatment scheme to compound 19. Remarkably, treatment with compound 19 was able to reduce infection under the detection limit. More so, no relapse was detected for 3 weeks after the treatment, suggesting that the animals were indeed cured. To confirm this possibility, the treated mice immune system was suppressed with cyclophosphamide. Once again no relapse was detected supporting the scenario of full parasite clearance upon treatment (FIG. 5). Treatments with miltefosine, instead did not work at all. The advantage over pentamidine is the oral administration of compound 19 versus ip administration of pentamidine.

Example 13

Evaluation of the Potential of 5-cyclonentadecyloentyl) (2-(trimethylammonio)ethyl) phosohate (19) to Work in a Stage II HAT Mice Model Using *T. b. brucei* GVR35

The potential of compound 19 to treat *T. brucei* chronic infection in conjunction with the fact that 5-cyclopentadecylpentyl) (2-(trimethylammonio)ethyl) phosphate (19) can be detected in the brain (Tables 10 and 11) supports a possible activity in stage II HAT. To address this, a more complex model of *T. brucei* mice infection that originates a chronic infection enabling the dissemination of the parasite into the brain was used. In this infection model the traditional stage I drugs like pentamidine are not able to clear infection (FIG. 6).

A preliminary experiment with 13 days treatment with compound 19 (50 mg/kg/day PO) reduced infection by >99%. The untreated animals were sacrificed at day 31 due to the infection reaching the humane end-point. As expected melarsoprol at 10 mg/kg/day IP was able to clear the infection after 7 days of treatment, while pentamidine (5 mg/kg/day IP) was not able to clear infection in the brain, with the animals being sacrificed at day 34 post infection due to the infection arrived to experimental humane end-point. Miltefosine treated animals showed no reduction in infection and presented constant weight loss associated to the treatment, that lead to the animals being sacrificed after 7 treatments due to general bad condition. Compound 19 was able to significantly reduce the overall infection and also in the brain. The reduction was already significant with just 4 administrations. The subsequent treatments were not able to fully clear infection in the brain that maintained a low but persistent signal (FIG. 6).

In conclusion, compound 19 was able to reduce infection in the brain. The behavior of compound 19 was distinct from pentamidine, a drug that does not cross the blood brain barrier. Therefore, compound 19 is a therapeutic option to stage II HAT.

Example 14

5-cyclopentadecylpentyl (2-(trimethylammonio) ethyl) phosphate (19) aggregates in saline solutions of NaCl producing a homogeneous gel product. This effect is more pronounced at concentrations between 7 and 40 mg/mL at a temperature range between 20° C. and 40° C., preferably at ambient temperature. The homogeneity of the product facilitates homogeneity of dosing, i.e., variability among doses is lower, easy administration of the compound and higher patient acceptability. This gel formation was not observed at the same conditions with other similar molecules such as miltefosine.

The invention claimed is:

1. A method of preventing and/or treating a protozoal disease in a mammal in need thereof, said method comprising:

administering an effective amount of compound 5-cyclopentadecylpentyl (2-(trimethylammonium) ethyl) phosphate having formula

19

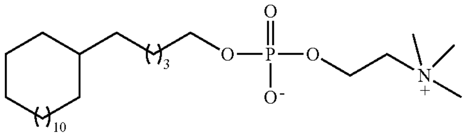

and a pharmaceutically acceptable carrier to said mammals wherein said compound maintains parasite burden below detection limit in spleen and liver of said mammal and said protozoal disease is leishmaniasis or African trypanosomiasis.

2. The method according to claim 1, wherein the mammal is a human.

3. The method according to claim 1, wherein the mammal is a non-human mammal.

4. The method according to claim 3, wherein the non-human mammal is a dog.

5. The method according to claim 1, wherein the compound is administered to the mammal orally, intranasally, intravenously, topically or intralesionally.

6. The method according claim 1, wherein the compound is administered to the mammal orally in a treatment course.

7. The method according to claim 1, wherein the compound is administered to the subject daily or every other day during the treatment course, and wherein the effective amount, administered as a single or divided dosages, is within the range from 1 mg/kg/day to 50 mg/kg/day bodyweight.

8. The method according to claim 1, wherein the protozoal disease is African Trypanosomiasis and wherein said compound is administered to the subject at an effective amount within the range from 20 mg/kg/day to 100 mg/kg/day bodyweight.

9. The method according to claim 1, wherein the pharmaceutical composition is formulated for oral, intranasal, intravenous, topical or intralesional administration.

10. The method according to claim 1, said pharmaceutical composition further comprising a drug delivery vehicle selected from the group comprising nanoparticles, liposomes, niosomes, microspheres or nanotubes, and one or more absorption enhancers.

11. The method according to claim 1 said pharmaceutical composition further comprising one or more active substances, wherein the one or more active substances are natural and/or synthetic substances.

12. The method according to claim 11, wherein the one or more active substances are selected from the group consisting of pentavalent antimonial preparations, amphotericin B, suramin, pentamidine, allopurinol, melarsoprol, benznidazol, nifurtimox, ketoconazol, difluoromethylornithine, chloroquine, quinine, immunostimulants and immunomodulatory agents.

13. The method-according to claim 1, wherein the pharmaceutically acceptable carrier comprises a saline solution, whereby said carrier interacts with the compound to form a gel composition.

14. The method according claim 6, wherein said treatment course has a duration of 3 days to 28 days.

15. The method according to claim 8, wherein said compound is administered for a period ranging from 3 to 7 days.

16. The method according to claim 10, said pharmaceutical composition further comprising natural and/or synthetic polymers.

* * * * *